(12) United States Patent  (10) Patent No.: US 9,149,194 B2
Sawanoi et al.  (45) Date of Patent: Oct. 6, 2015

(54) ELECTRONIC SPHYGMOMANOMETER

(75) Inventors: Yukiya Sawanoi, Nara (JP); Yoshihide Tokko, Kyoto (JP)

(73) Assignee: OMRON HEALTHCARE Co., Ltd., Kyoto (JP)

( * ) Notice: Subject to any disclaimer, the term of this patent is extended or adjusted under 35 U.S.C. 154(b) by 1083 days.

(21) Appl. No.: 13/213,590

(22) Filed: Aug. 19, 2011

(65) Prior Publication Data

US 2011/0301476 A1  Dec. 8, 2011

Related U.S. Application Data

(63) Continuation of application No. PCT/JP2010/051696, filed on Feb. 5, 2010.

(30) Foreign Application Priority Data

Feb. 25, 2009  (JP) ................................. 2009-042605

(51) Int. Cl.
*A61B 5/0225* (2006.01)
*A61B 5/022* (2006.01)

(52) U.S. Cl.
CPC .............. *A61B 5/022* (2013.01); *A61B 5/02225* (2013.01); *A61B 2560/0261* (2013.01)

(58) Field of Classification Search
USPC .......................................... 600/490, 492, 494
See application file for complete search history.

(56) References Cited

U.S. PATENT DOCUMENTS

| 5,746,698 A | * | 5/1998 | Bos et al. | 600/493 |
| 6,120,459 A | * | 9/2000 | Nitzan et al. | 600/493 |
| 2004/0024324 A1 | * | 2/2004 | Bratteli | 600/490 |

FOREIGN PATENT DOCUMENTS

| JP | 61-247431 A | 11/1986 |
| JP | 62-072606 U | 5/1987 |
| JP | 07-136133 A | 5/1995 |
| JP | 2001-008908 A | 1/2001 |
| WO | 02/39893 A1 | 5/2002 |

OTHER PUBLICATIONS

International Search Report issued in PCT/JP2010/051696 mailed on Mar. 9, 2010, with English translation thereof, 7 pages.
Patent Abstracts of Japan, Publication No. 07-136133, Publication Date: May 30, 1995, 1 page.

(Continued)

*Primary Examiner* — Patricia Mallari
*Assistant Examiner* — Michael Catina
(74) *Attorney, Agent, or Firm* — Osha Liang LLP

(57) ABSTRACT

In a sphygmomanometer for measuring blood pressure according to a volume compensation method, an upper arm V0 equivalent cuff pressure representing a cuff pressure in a state where an inner pressure and an outer pressure of an artery of an upper arm are in equilibrium is specified based on a cuff pressure signal of the upper arm. For example, the upper arm V0 equivalent cuff pressure is detected as an average blood pressure obtained from the cuff pressure signal of the upper arm. After a control target value and an initial cuff pressure in the volume compensation are detected, a difference between the initial cuff pressure and the upper arm V0 equivalent cuff pressure is calculated as a correction value, and the blood pressure value in the volume compensation method is corrected with the calculated correction value.

3 Claims, 20 Drawing Sheets

(56) References Cited

OTHER PUBLICATIONS

Patent Abstracts of Japan, Publication No. 63-247431, Publication Date: Oct. 14, 1988, 1 page.
Patent Abstracts of Japan, Publication No. 2001-008908, Publication Date: Jan. 16, 2001, 1 page.
Imholz et al, "Feasability of Ambulatory, Continuous 24-Hour Finger Arterial Pressure Recording," Hypertension, vol. 21, No. 1, Jan. 1993, 9 pages.
Office Action issued in corresponding Japanese Application No. 2009-042605 dated Jan. 15, 2013, and English translation thereof (8 pages).

* cited by examiner

ELECTRONIC SPHYGMOMANOMETER

TECHNICAL FIELD

The present invention relates to electronic sphygmomanometers, and in particular, to an electronic sphygmomanometer that uses a site other than the upper arm as a measurement site.

BACKGROUND ART

Blood pressure is one type of index for analyzing cardiovascular diseases, and performing risk analysis based on the blood pressure is effective in preventing cardiovascular related diseases such as apoplexy, heart failure, cardiac infarct, and the like. In particular, the early morning high blood pressure in which the blood pressure rises in early morning is related to heart disease and apoplexy. Moreover, among the early morning high blood pressure, a symptom in which the blood pressure rapidly rises within one hour or one and a half hours after waking up called the "morning surge" is known to have a cause and effect relationship with apoplexy. Thus, it is useful in risk analysis of cardiovascular related disease to grasp the mutual relationship between time (lifestyle habit) and change in blood pressure. Therefore, the blood pressure measurement needs to be carried out continuously over a long period. In monitoring of patients during surgery and after surgery, in checking medicinal effect when treating with antihypertensive medication, and the like, it is very important to continuously measure the blood pressure for every heart beat and to monitor the change in blood pressure.

In sphygmomanometers that are commercially available and that are being developed, the measurement site includes a wide range of sites such as the upper arm, wrist, finger, and ear. When measuring the blood pressure, the height of the measurement site needs to be the same as the height of the heart. If there is a difference in height between the measurement site and the heart, a differential pressure is generated in the blood pressure of the measurement site and the heart due to such difference, and the measured blood pressure value may be inaccurate.

As described in Japanese Unexamined Patent Publication No. 7-136133 (patent document 1) and "Feasibility of ambulatory, continuous 24-hour finger arterial pressure recording" by B P Imholz et al., Hypertension, American Heart Association, January 1993, $21^{st}$ volume, $1^{st}$ section, P. 65 to 73 (non patent document 1), the measurement site such as the finger and the heart position are connected with a tube filled with liquid having substantially the same specific gravity as blood, the pressure difference is measured, and the blood pressure value is corrected.

As described in WO 2002/039893 pamphlet (patent document 2), a sphygmomanometer that uses the wrist for the measurement site includes a sphygmomanometer having a function of guiding the height of the wrist so as to become equal to the height of the heart by a height sensor incorporated therein.

Patent Document 1: Japanese Unexamined Patent Publication No. 7-136133
Patent Document 2: WO 2002/039893 pamphlet
Non-Patent Document 1: "Feasibility of ambulatory, continuous 24-hour finger arterial pressure recording" by B P Imholz et al., Hypertension, American Heart Association, January 1993, $21^{st}$ volume, $1^{st}$ section, P. 65 to 73

SUMMARY OF INVENTION

In the method of correcting the blood pressure value of the related art, the change in height of the measurement site can be followed, but the tube for connecting the measurement site and the heart position is necessary.

Furthermore, mounting the guide function of the height as in WO 2002/039893 pamphlet (patent document 2) is an effective solution for the wrist, the finger, and the like where the height of the measurement site can be adjusted, but is not a solution to the sphygmomanometer for a site where the height of the measurement site cannot be adjusted such as the ear.

Therefore, one or more embodiments of the present invention provides an electronic sphygmomanometer, which uses a site (peripheral site) other than the upper arm as a measurement site, capable of accurately measuring the blood pressure without arranging a special hardware.

According to one or more embodiments of the present invention, there is provided an electronic sphygmomanometer having a peripheral site as a measurement site; the electronic sphygmomanometer including a first cuff to be wrapped around the peripheral site; a second cuff to be wrapped around an upper arm; a pressure detection unit for detecting a first cuff pressure signal representing a pressure of the first cuff and a second cuff pressure signal representing a pressure of the second cuff; a specific processing unit for carrying out a process for specifying an upper arm equilibrium value representing a cuff pressure in a state where an inner pressure and an outer pressure of an artery of the upper arm are in equilibrium based on the second cuff pressure signal; and a measurement control unit for measuring a blood pressure of a person to be measured based on the first cuff pressure signal; wherein the measurement control unit carries out a control for correcting a blood pressure value obtained according to the first cuff pressure signal so that a peripheral equilibrium value representing a cuff pressure in a state where an inner pressure and an outer pressure of an artery of the peripheral site are in equilibrium matches with the upper arm equilibrium value.

According to one or more embodiments of the present invention, there is further arranged a first volume detection unit, arranged at a predetermined position of the first cuff, for detecting a first arterial volume signal at the peripheral site; wherein the measurement control unit carries out an arterial volume constant control based on the first arterial volume signal to continuously measure the blood pressure; and the peripheral equilibrium value corresponds to an initial cuff pressure representing a reference value of the first cuff pressure signal in the arterial volume constant control.

According to one or more embodiments of the present invention, the measurement control unit detects a maximum value of a volume change signal of the peripheral site from the first arterial volume signal in a process of gradually pressurizing or depressurizing the pressure of the first cuff to detect a volume value in a state where the inner pressure and the outer pressure of the artery of the peripheral site are in equilibrium as a control target value in the arterial volume constant control and to detect a value of the first cuff pressure signal corresponding to a time point when the control target value is detected as the initial cuff pressure. The cuff pressure obtained when a difference between the value of the first arterial volume signal and the control target value becomes smaller than or equal to a predetermined value when the arterial volume constant control is carried out is determined as a temporary blood pressure value; and the temporary blood pressure value is corrected according to a difference between the upper arm equilibrium value and the initial cuff pressure.

According to one or more embodiments of the present invention, the measurement control unit detects a control target value in the arterial volume constant control with the pressure of the first cuff fixed at the upper arm equilibrium value, the upper arm equilibrium value being the initial cuff pressure, and determines the cuff pressure obtained when a difference between the value of the first arterial volume signal and the control target value becomes smaller than or equal to a predetermined value when the arterial volume constant control is carried out as the blood pressure value.

According to one or more embodiments of the present invention, the specific processing unit specifies either an average blood pressure obtained from the second cuff pressure signal or the cuff pressure at a time point when a maximum value of the amplitude of a pressure pulse wave is detected as the upper arm equilibrium value.

According to one or more embodiments of the present invention, a second volume detection unit, arranged at a predetermined position of the second cuff, for detecting a second arterial volume signal at the upper arm is further arranged; wherein the specific processing unit specifies the upper arm equilibrium value by detecting a maximum value of an arterial volume change of the upper arm from the second arterial volume signal in the process of gradually pressurizing or depressurizing the pressure of the second cuff.

According to one or more embodiments of the present invention, the measurement control unit calculates a temporary blood pressure value based on an amplitude of a pressure pulse wave corresponding to the first cuff pressure signal, and corrects the temporary blood pressure value according to a difference between the peripheral equilibrium value and the upper arm equilibrium value.

According to one or more embodiments of the present invention, the peripheral equilibrium value is defined in advance to be an average blood pressure obtained from the first cuff pressure signal or a cuff pressure at a time point when a maximum value of an amplitude of a pressure pulse wave is detected.

According to one or more embodiments of the present invention, the specific processing unit specifies either an average blood pressure obtained from the second cuff pressure signal or the cuff pressure at a time point when a maximum value of the amplitude of a pressure pulse wave is detected as the upper arm equilibrium value.

According to one or more embodiments of the present invention, a volume detection unit, arranged at a predetermined position of the second cuff, for detecting an arterial volume signal at the upper arm is further arranged; wherein the specific processing unit specifies the upper arm equilibrium value by detecting a maximum value of an arterial volume change of the upper arm from the arterial volume signal in the process of gradually pressurizing or depressurizing the pressure of the second cuff.

According to one or more embodiments of the present invention, the blood pressure can be accurately measured without arranging a special hardware even with a sphygmomanometer having the peripheral site as a measurement site.

DETAILED DESCRIPTION OF INVENTION

Figure 1:
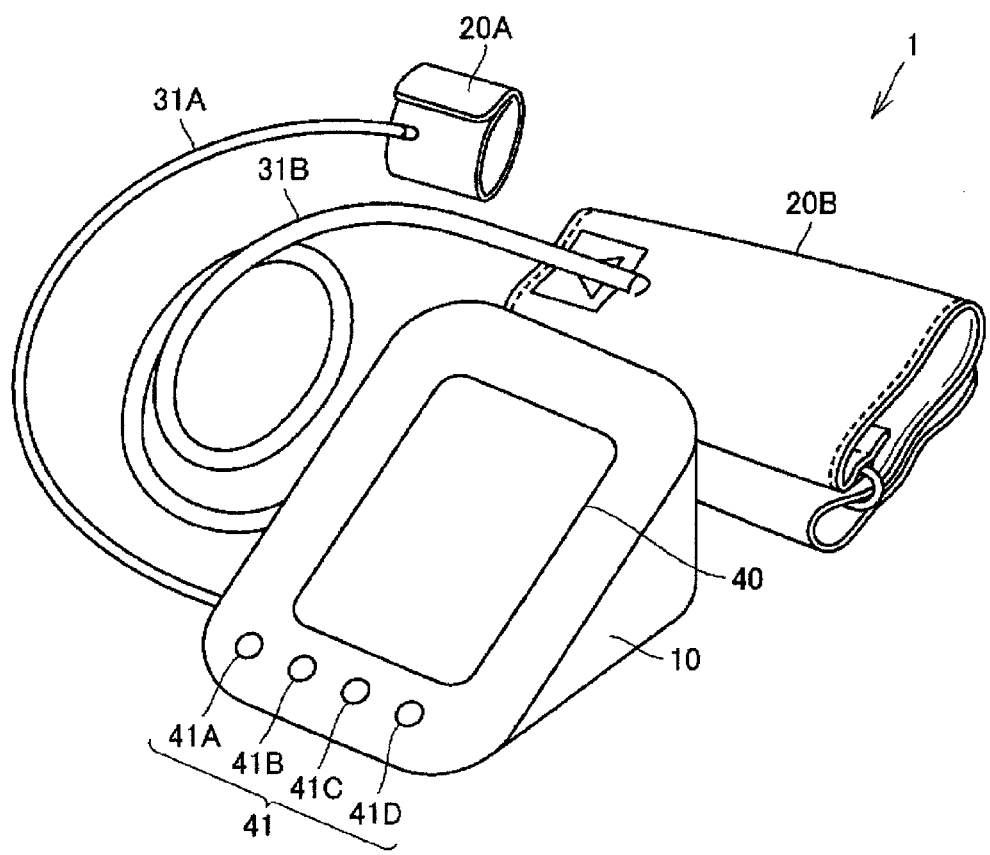
FIG. 1 is a perspective view of an outer appearance of a sphygmomanometer according to one or more embodiments of the present invention.

Embodiments of the present invention will be described in detail with reference to the drawings. The same reference numerals are denoted for the same or equivalent portions in the figures, and the description thereof will not be repeated.

[First Embodiment]

<Outer Appearance and Configuration>

First, the outer appearance and the configuration of an electronic sphygmomanometer (hereinafter abbreviated as "sphygmomanometer") according to a first embodiment of the present invention will be described.

(Regarding Outer Appearance)

With reference to FIG. 1, a sphygmomanometer 1 includes a main body 10, two cuffs 20A, 20B and two air tubes 31A, 31B.

The cuff 20A can be attached to a peripheral site of a person to be measured that is a measurement site of the blood pressure. The cuff 20B can be attached to an upper arm of the person to be measured. The air tube 31A connects the main body 10 and the cuff 20A. The air tube 31B connects the main body 10 and the cuff 20B.

In the present embodiment, "peripheral site" refers to the site other than the upper arm (e.g., wrist, finger, ear, etc.) of the physical sites at which the blood pressure can be measured. The peripheral site is assumed as the wrist in the following description.

Hereinafter, the cuff 20A is also referred to as "measurement cuff 20A", and the cuff 20B is also referred to as "upper arm cuff 20B".

A display unit 40 configured by, for example, liquid crystals, and an operation unit 41 for accepting instructions from the user (representatively person to be measured) are arranged on a surface of the main body 10.

The operation unit 41 includes, for example, a power supply switch 41A for accepting an input of instruction to turn ON or OFF the power supply, a measurement switch 41B for accepting instruction to start the measurement, a stop switch 41C for accepting instruction to stop the measurement, and a memory switch 41D for accepting instruction to read out stored values (measurement data).

In the present embodiment, the tube 31B connected to the upper arm cuff 20B and the tube 31A connected to the measurement cuff 20A may be removable with respect to the main body 10.

(Regarding Hardware Configuration)

Figure 2:
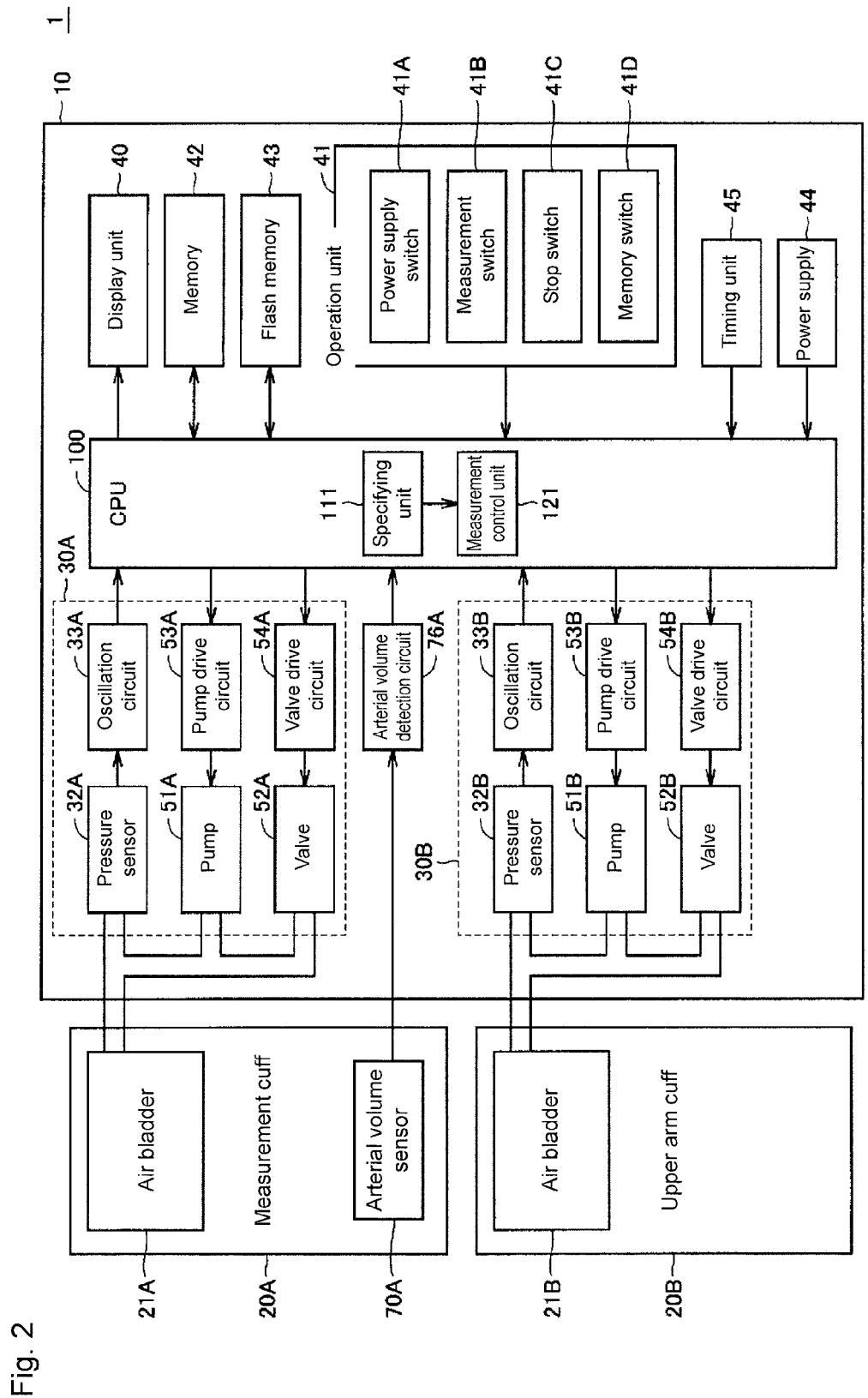
FIG. 2 is a block diagram showing a hardware configuration of the sphygmomanometer according to a first embodiment of the present invention.

With reference to FIG. 2, the sphygmomanometer 1 according to the present embodiment continuously measures the blood pressure according to a volume compensation method.

The measurement cuff 20A includes an air bladder 21A and an arterial volume sensor 70A for detecting the volume of the artery at the measurement site (wrist).

The arterial volume sensor 70A is configured by a light emitting element and a light receiving element (not shown). The light emitting element irradiates the artery with light, and the light receiving element receives the light (transmitted light) in which the light applied by the light emitting element is transmitted through the artery or the light (reflected light) reflected by the artery. The light emitting element and the light receiving element are, for example, arranged at a predetermined interval on the inner side of the air bladder 21A.

Alternatively, the arterial volume sensor 70A may detect the volume of the artery by an impedance sensor (impedance plethysmograph). In such a case, the arterial volume sensor 70A is to be configured by a plurality of electrodes (electrode pair of current application and electrode pair for voltage detection) for detecting the impedance of the site including the artery.

The upper arm cuff 20B includes an air bladder 21B.

In addition to the display unit 40 and the operation unit 41, the main body 10 includes a CPU (Central Processing Unit) 100 for controlling each unit in a concentrated manner, and carrying out various types of calculation processes, a memory unit 42 for storing various types of programs and data, a nonvolatile memory (e.g., flash memory) 43 for storing the measurement data, a power supply 44 for supplying power to the CPU 100, and the like, a timing unit 45 for carrying out the timing operation, an arterial volume detection circuit 76A connected to the arterial volume sensor 70A, a measurement air system 30A, and an upper arm air system 30B.

The arterial volume detection circuit 76A is, for example, configured by a drive circuit (not shown) for causing a light emitting element (not shown) to emit light at a predetermined timing according to a command signal from the CPU 100, and a detection circuit (not shown) for detecting the arterial volume of the measurement site by converting the output from a light receiving element (not shown) to a voltage value.

The air system 30A includes a pressure sensor 32A, a pump 51A, a valve 52A, an oscillation circuit 33A, a pump drive circuit 53A, and a valve drive circuit 54A.

The pressure sensor 32A is a device for detecting the pressure (cuff pressure) of the air bladder 21A. The pump 51A supplies air to the air bladder 21A to pressurize the cuff 20A. The valve 52A is opened and closed to discharge or enclose the air of the air bladder 21A.

The pressure sensor 32A is, for example, a capacitance type pressure sensor in which the capacitance value changes according to the cuff pressure. The oscillation circuit 33A outputs a signal of the oscillating frequency corresponding to the capacitance value of the pressure sensor 32A to the CPU 100. The CPU 100 converts the signal obtained from the oscillating circuit 33A to pressure, and detects the pressure. The pump drive circuit 53A controls the drive of the pump 51A based on the control signal provided from the CPU 100. The valve drive circuit 54A carries out the open/close control of the valve 52A based on the control signal provided from the CPU 100.

The air system 30B includes a pressure sensor 32B, a pump 51B, a valve 52B, an oscillation circuit 33B, a pump drive circuit 53B, and a valve drive circuit 54B. These hardware are similar to the air system 30A, and hence, the description thereof will not be repeated.

In the present embodiment, the air systems 30A, 30B are arranged for the measurement cuff 20A and the upper arm cuff 20B, respectively, but a common air system may be arranged to change the pressure adjusting target.

The pressure adjustment unit for adjusting the pressure of the cuffs 20A, 20B by pressurization and depressurization is not limited to the pumps 51A, 51B, the valves 52A, 52B, the pump drive circuits 53A, 53B, and the valve drive circuits 54A, 54B. For instance, the pressure adjustment unit for the cuff 20A may include an air cylinder and an actuator for driving the air cylinder in addition to/in place of the hardware described above.

The cuffs 20A, 20B are pressurized and depressurized by air, but the fluid supplied to the cuffs 20A, 20B is not limited to air and may be liquid or gel. Alternatively, it is not limited to fluid and may be uniform microscopic particles such as micro-beads.

(Regarding Volume Compensation Method)

The blood pressure measurement method by the volume compensation method will be briefly described below.

The volume compensation method is a method of compressing the artery with a cuff from outside the living body, making the pressure (cuff pressure) for compressing the measurement site and the inner pressure of the artery of the measurement site, that is, the blood pressure equilibrium by constantly maintaining the volume of the artery that pulsates in synchronization with the heart beat constant, and continuously obtaining the blood pressure value by detecting the cuff pressure when the equilibrium state is maintained.

Figure 3:
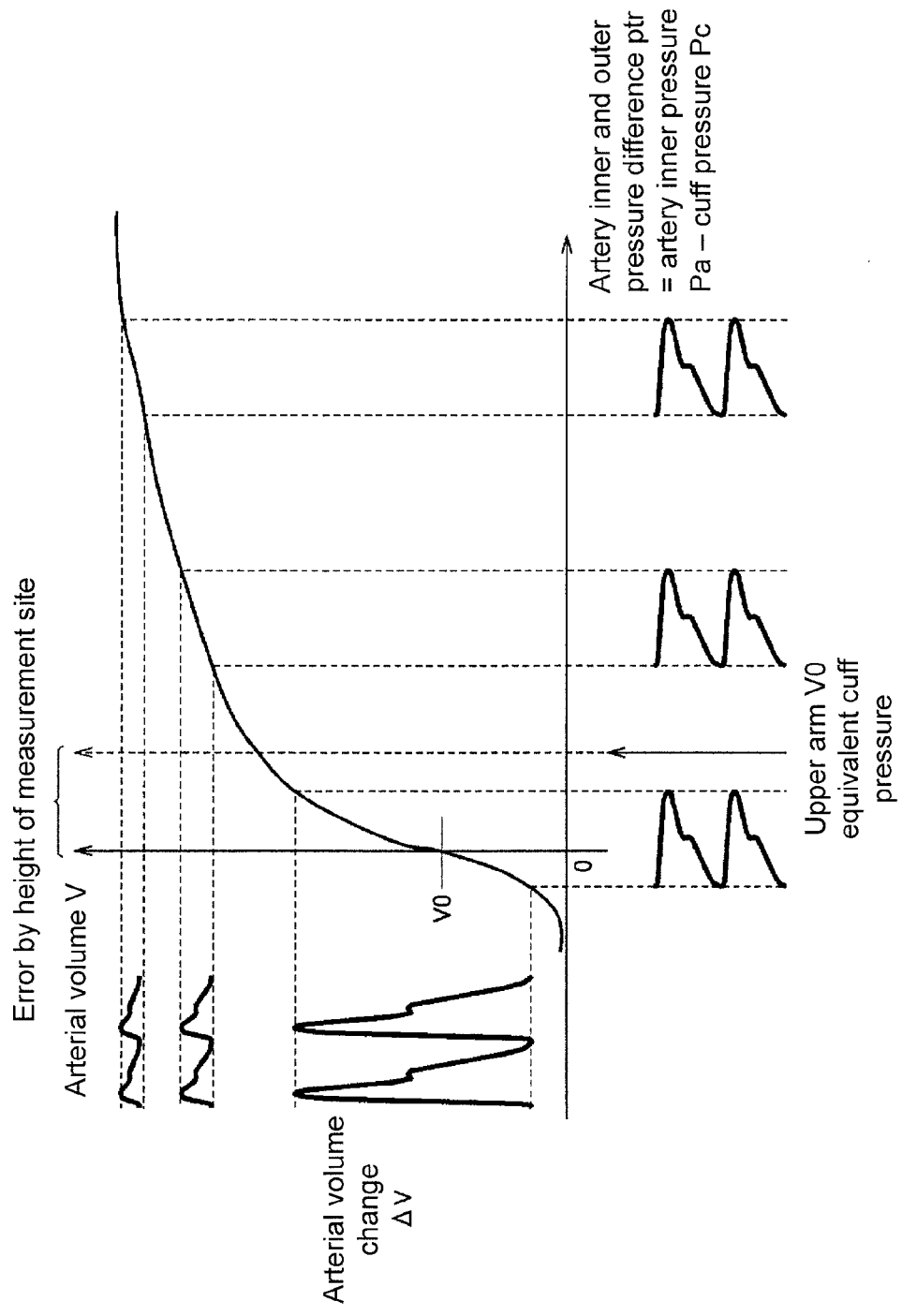
FIG. 3 is a graph showing mechanical characteristics of the artery.

The graph showing the mechanical characteristics of the artery of FIG. 3 shows the relationship of the artery inner and outer pressure difference Ptr and the arterial volume V, where the artery inner and outer pressure difference Ptr is shown on the horizontal axis and the arterial volume V is shown on the vertical axis. The artery inner and outer pressure difference Ptr indicates the difference between the artery inner pressure Pa and the cuff pressure Pc applied by the cuff from outside the living body.

As shown on the graph, the mechanical characteristics of the artery typically indicate a strong nonlinearity, where the compliance of the artery (amount of change in volume by pulsation) becomes a maximum when the artery inner and outer pressure difference Ptr is 0 (equilibrium state), that is, when the artery wall is in the no-load state. In other words, the follow-up property (development property) of the volume change with respect to the pressure change becomes a maximum. In the volume compensation method, the blood pressure is measured by sequentially controlling the ex vivo pressure (cuff pressure) so that the detected arterial volume always becomes a capacitance value of the time point when the artery inner and outer pressure difference Ptr becomes 0. To this end, the capacitance value V0 of the time point when the artery inner and outer pressure difference Ptr becomes 0 (state in which the inner pressure and the outer pressure of the artery of the measurement site are in equilibrium) is detected as a "control target value" prior to the blood pressure measurement. The cuff pressure at the time point when the capacitance value V0 is detected is detected as a "control initial cuff pressure". In the present embodiment, the cuff pressure is also referred to as "V0 equivalent cuff pressure of measurement site".

However, the blood pressure value contains error even if the capacitance value V0 is accurately detected if the position of the measurement site does not match with the height of the heart.

The shift with the height of the heart is less likely to occur if the measurement site is the upper arm, but high speed responsiveness of the cuff pressure is generally necessary when measuring the blood pressure with the volume compensation method. Thus, the peripheral site such as the wrist is used for the measurement site to miniaturize the pressurization and depressurization mechanism. Therefore, the user needs to bring the measurement site to the height of the heart, where the cuff pressure (control initial pressure) at the time point when the artery inner and outer pressure difference Ptr becomes 0 becomes higher than the cuff pressure obtained when the measurement site matches with the height of the heart if the measurement site is lower than the height of the heart. If the measurement site is shifted upward than the height of the heart, the cuff pressure (control initial pressure) at the time point when the artery inner and outer pressure difference Ptr becomes 0 becomes lower than the cuff pressure obtained when the measurement site matches with the height of the heart. Thus, when measuring the cuff pressure obtained when the arterial volume matches with the control target value (V0) as the blood pressure, the blood pressure cannot be accurately measured if the height of the measurement site is shifted from the position of the heart.

If the measurement site is the upper arm, on the other hand, error caused by the shift in height is less likely to occur. The sphygmomanometer 1 according to the present embodiment thus performs a process of correcting the error caused by the shift in height using the upper arm V0 equivalent cuff pressure. The "upper arm V0 equivalent cuff pressure" is the cuff pressure in a state where the inner pressure and the outer pressure of the artery of the upper arm are in equilibrium.

FIG. 3 shows the error of the upper arm V0 equivalent cuff pressure and the V0 equivalent cuff pressure of the measurement site when the height of the measurement site is shifted to lower than the position of the heart.

(Regarding Function Configuration)

The block diagram of FIG. 2 also shows the function configuration of the CPU 100. The CPU 100 includes a specifying unit 111 and a measurement control unit 121 as functions thereof.

The specifying unit 111 performs a process for specifying the upper arm V0 equivalent cuff pressure based on the cuff pressure signal of the upper arm output from the oscillation circuit 33B. For example, the specifying unit 111 specifies an average blood pressure calculated based on the cuff pressure signal of the upper arm as the upper arm V0 equivalent cuff pressure.

The measurement control unit 121 performs the control of measuring the blood pressure of the person to be measured based on the cuff pressure signal of the measurement site output from the oscillation circuit 33A. Furthermore, the measurement control unit 121 performs the control for correcting the blood pressure value obtained according to the cuff pressure signal of the measurement site so that the V0 equivalent cuff pressure of the measurement site matches with the upper arm V0 equivalent cuff pressure.

The sphygmomanometer 1 according to the present embodiment continuously measures the blood pressure according to the volume compensation method, so that the V0 equivalent cuff pressure of the measurement site corresponds to the control initial cuff pressure in the servo control (arterial volume constant control).

Therefore, in the present embodiment, the measurement control unit 121 performs the following processes. In other words, when the servo control is performed, the cuff pressure obtained when the difference between the value of the arterial volume signal obtained from the arterial volume detection circuit 76A and the control target value becomes smaller than or equal to a predetermined value is determined as a temporary blood pressure value. The determined temporary blood pressure value is corrected according to the difference between the upper arm V0 equivalent cuff pressure and the control initial cuff pressure. The blood pressure value after the correction is output as the measurement result. That is, for example, the blood pressure value after the correction is displayed on the display unit 40 and/or stored in the flash memory 43.

The functions of the specifying unit 111 and the measurement control unit 121 may be realized by executing the software stored in the memory unit 42, or at least one part may be realized by hardware.

<Regarding Operation>

The operation of the sphygmomanometer 1 according to the present embodiment will now be described.

(Blood Pressure Measurement Process)

Figure 4:
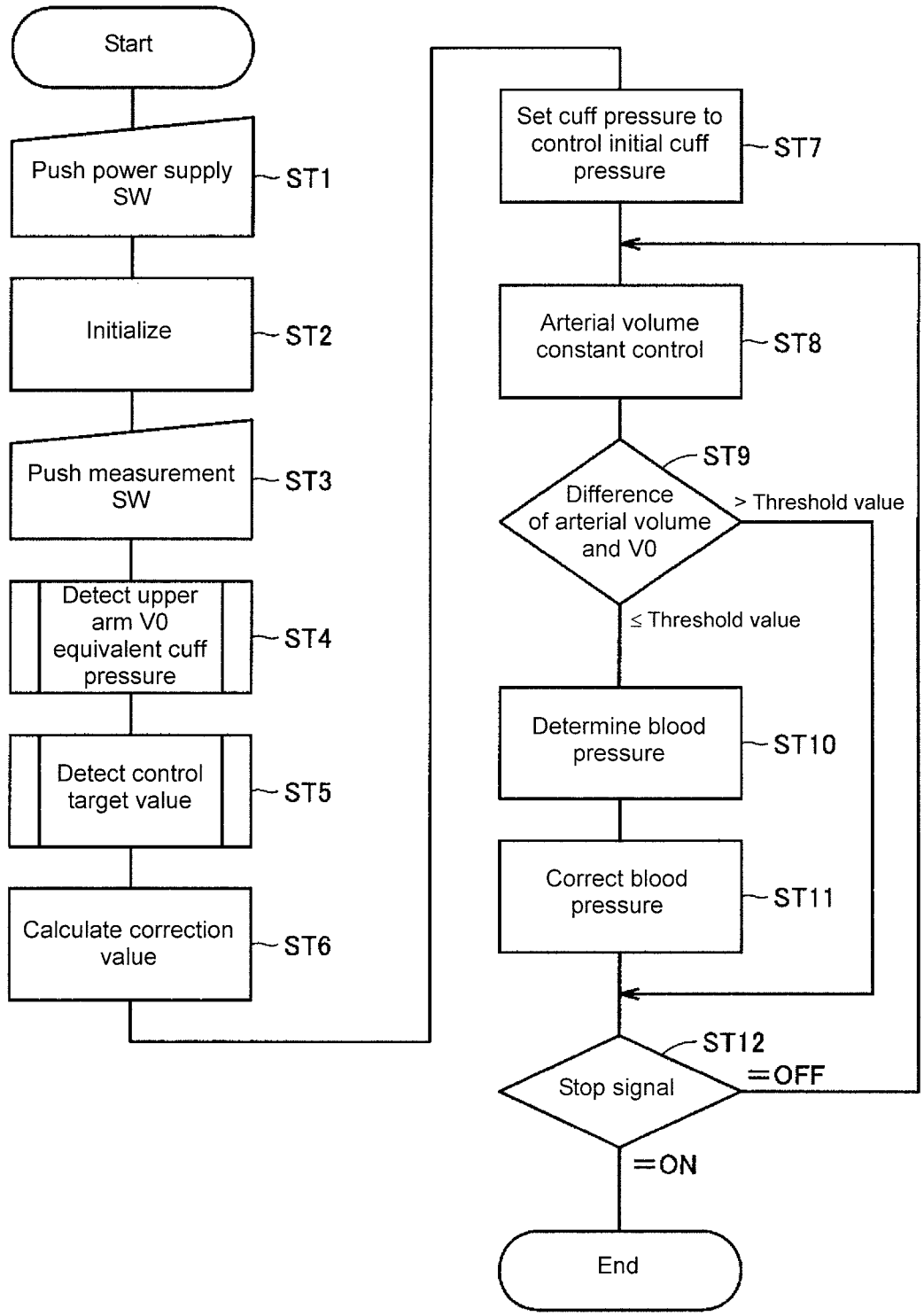
FIG. 4 is a flowchart showing a blood pressure measurement process in the first embodiment of the present invention.

The blood pressure measurement process in the first embodiment of the present invention will be described with reference to the flowchart of FIG. 4. The processes shown in the flowchart of FIG. 4 are stored in the memory unit 42 in advance as a program, and the function of the blood pressure measurement process is realized when the CPU 100 reads out the program and executes the same.

The CPU 100 performs the initialization process (ST2) when detecting that the power supply switch 41A is pushed (ST1). Specifically, a predetermined region of the memory unit 42 is initialized, the air of the air bladders 21A and 21B is exhausted, and the 0 mmHg correction of the pressure sensors 32A and 32B is carried out.

After the initialization is finished, the CPU 100 determines whether or not the measurement switch 41B is pushed. If the measurement switch 41B is pushed (ST3), the specifying unit 111 executes the detection process of the upper arm V0 equivalent cuff pressure (ST4). This process will be described in detail later.

The measurement control unit 121 then executes a control target value detection process (ST5). In the present embodiment, the control target value (V0) and the control initial cuff pressure are determined through a known method. This process will also be described in detail later.

The order of executing the process of step ST4 and the process of step ST5 is not relevant.

The measurement control unit 121 then calculates the correction value of the blood pressure (ST6). The correction value is calculated with the following equation.

Correction value=control initial cuff pressure−upper arm $V0$ equivalent cuff pressure Then, the cuff inner pressure is adjusted so that the cuff pressure signal of the measurement site matches with the control initial cuff pressure (ST7). The control initial cuff pressure becomes a reference value of the cuff pressure signal of the measurement site in the arterial volume constant control.

Thereafter, the cuff pressure is feedback controlled so that the difference between the arterial volume signal and the control target value (V0) becomes a minimum (ST8). That is, the arterial volume constant control is carried out. In this case, the cuff pressure obtained when the difference between the arterial volume signal and the control target value becomes smaller than a predetermined value (threshold value) is determined as the temporary blood pressure value (ST9, ST10).

The measurement control unit 121 corrects the temporary blood pressure value determined in the above manner with the correction value obtained in step ST6 (ST11). The correction of the blood pressure is calculated with the following equation.

Blood pressure value=volume compensation method blood pressure−correction value

The feedback control is continued until the stop signal is turned ON by input of the stop switch 41C, elapse of a predetermined time, or the like (ST12).

Therefore, in the present embodiment, the (temporary) blood pressure value is measured once with a normal measurement method in the volume compensation method. The blood pressure value is then corrected with the blood pressure obtained when measured with the upper arm as the reference. That is, the blood pressure value in the volume compensation method is corrected according to the difference between the upper arm V0 equivalent cuff pressure and the V0 equivalent cuff pressure of the measurement site. Therefore, even if the height of the measurement site is shifted from the position of the heart, the error caused by such shift can be reduced. As a result, the blood pressure value can be accurately measured even if the measurement site is a peripheral site.

(Control Target Value Detection Process)

Figure 5:
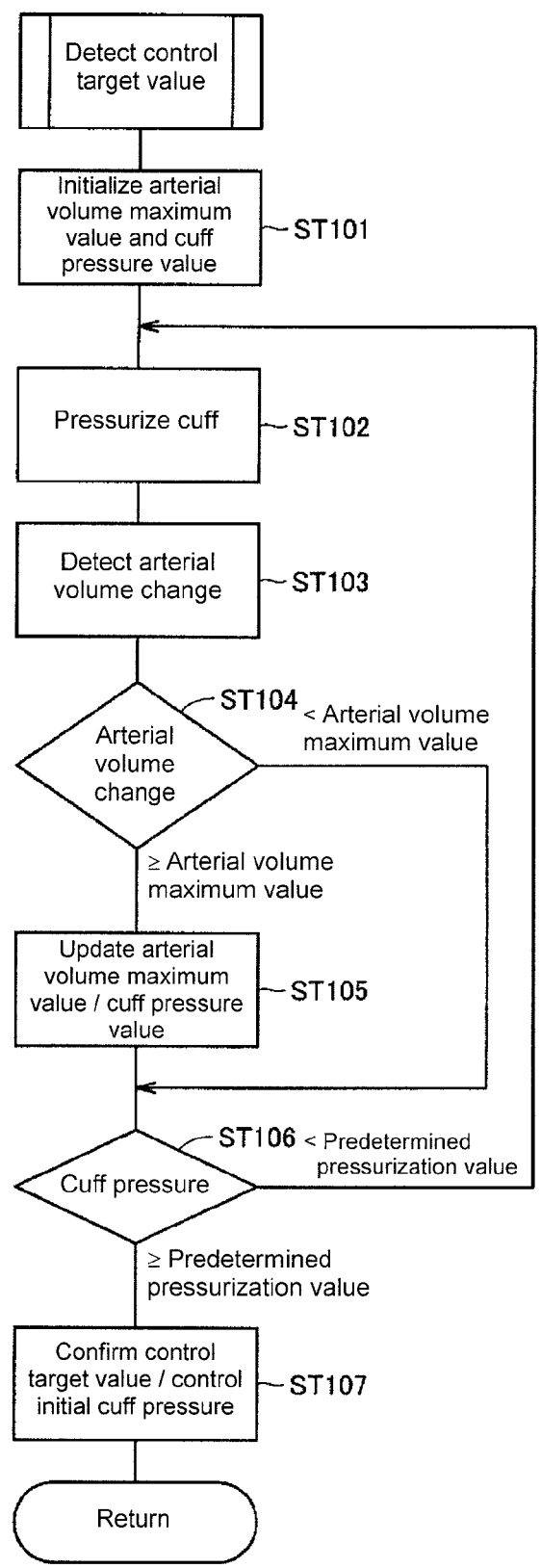
FIG. 5 is a flowchart showing a control target value detection process in the first embodiment of the present invention.

With reference to FIG. 5, the measurement control unit 121 initializes the memory region (e.g., predetermined region of memory unit 42) for storing the maximum value of the arterial volume change (hereinafter also referred to as "arterial volume maximum value") and the cuff pressure at the relevant time (ST101).

The pump drive circuit 53A is then drive-controlled to gradually pressurize the pressure of the measurement cuff 20A at low speed of about 3 mmHg/sec (ST102).

During the pressurization, the measurement control unit 121 detects a signal (arterial volume signal) from the arterial volume detection circuit 76A (ST103). The measurement control unit 121 detects the arterial volume change signal indicating the amount of change for every beat of the arterial volume signal. The arterial volume change signal can be obtained by filter-processing the arterial volume signal, for example. Both the arterial volume signal and the arterial volume change signal may be detected in the arterial volume detection circuit 76A.

The value of the arterial volume signal is assumed to be stored in time series in correspondence with the cuff pressure during the pressurization.

The measurement control unit 121 determines whether or not the detected arterial volume change is a maximum (ST104). If determined that the detected arterial volume change is a maximum ("≥arterial volume maximum value" in ST104), the measurement control unit 121 updates the maximum value of the arterial volume change and the cuff pressure of the relevant time (ST105). After such process is finished, the process proceeds to step ST106.

If determined that the detected arterial volume change is not a maximum in step ST104 ("<arterial volume maximum value" in step ST104), the process of step ST105 is skipped and the process proceeds to step ST106.

In step ST106, the measurement control unit 121 determines whether or not the cuff pressure is greater than or equal to a predetermined value (e.g., 180 mmHg). If determined that the cuff pressure has not reached the predetermined value ("<predetermined pressurization value" in ST106), the process returns to step ST102 and the above processes are repeated. If determined that the cuff pressure has reached the predetermined value ("≥predetermined pressurization value" in ST106), the process proceeds to step ST107.

In step ST107, the measurement control unit 121 confirms the average value of the arterial volume signal for one beat corresponding to the maximum arterial volume change as the control target value (V0). More specifically, the arterial volume signal for one beat when the arterial volume change is a maximum is specified by the cuff pressure stored in a predetermined memory region. The average value of the specified arterial volume signal for one beat is calculated as the control target value. The measurement control unit 121 then confirms the cuff pressure at the relevant time, that is, the cuff pressure stored in a predetermined memory region as the control initial cuff pressure.

After the process of ST107 is finished, the process returns to the main routine.

Figure 6:
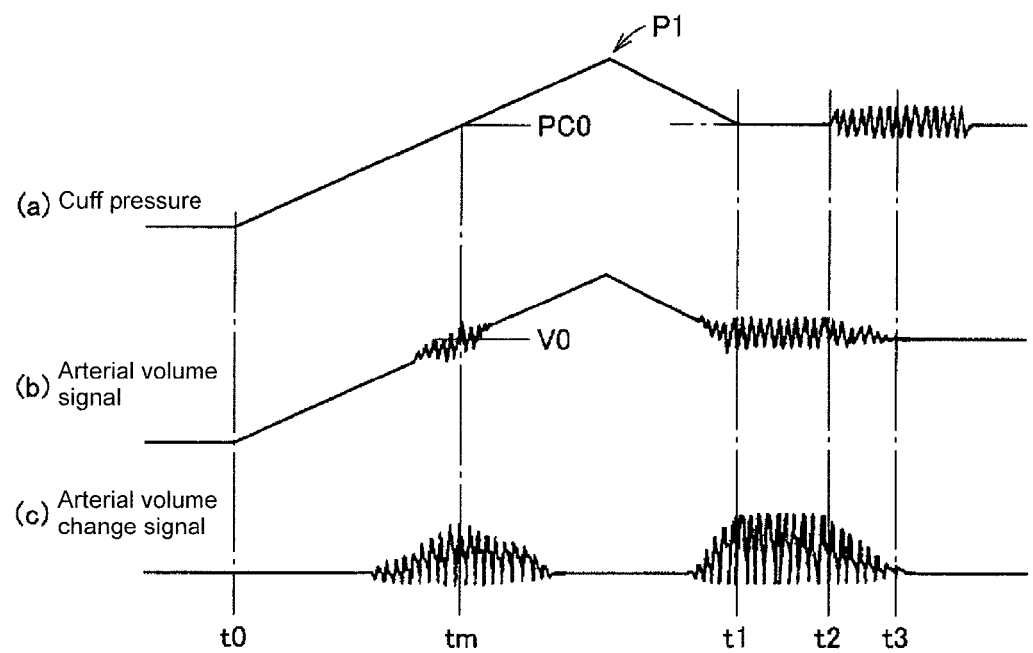
FIG. 6 is a view describing a detection method of a control target value and a control initial cuff pressure (initial cuff pressure) according to a first embodiment of the present invention.

With reference to FIG. 6, the detection of the control target value and the control initial cuff pressure in the present embodiment will be more specifically described. FIG. 6(A) shows the cuff pressure of the measurement cuff 20A along the time axis. FIG. 6(B) shows the arterial volume signal of the measurement site along the time axis same as FIG. 6(A). FIG. 6(C) shows the arterial volume change signal of the measurement site along the time axis same as FIG. 6(A).

With reference to FIG. 6, the maximum value of the arterial volume change signal is detected in the process of pressurizing the cuff pressure at a constant speed to a predetermined value P1. The time point at which the maximum value of the arterial volume signal is detected is represented with time tm. For example, the average value of the arterial volume signal at time tm is detected as the control target value (V0). Further, the cuff pressure at time tm is detected as the control initial cuff pressure (PC0).

When the control target value and the control initial cuff pressure are detected in such manner, the cuff pressure is set to the control initial cuff pressure (PC0) as described above (ST7 of FIG. 4). The time point at which the cuff pressure is set to the control initial cuff pressure is indicated as time t1. Thereafter (time t2), the adjustment of the control gain is started and the optimum control gain is determined. The arterial volume constant control is then started (ST8 of FIG. 4). In the arterial volume constant control shown after time t3, the fine tuning of the pressure of the measurement cuff 20A is carried out such that the value of the arterial volume signal of the measurement site matches with the control target value.

The cuff pressure obtained as a result is determined as the (temporary) blood pressure value.

(One Example of Detection Process of Upper Arm V0 Equivalent Cuff Pressure)

In the present embodiment, the specifying unit 111 specifies the average blood pressure calculated using the air system 30B for the upper arm as the upper arm V0 equivalent cuff pressure.

Figure 7:
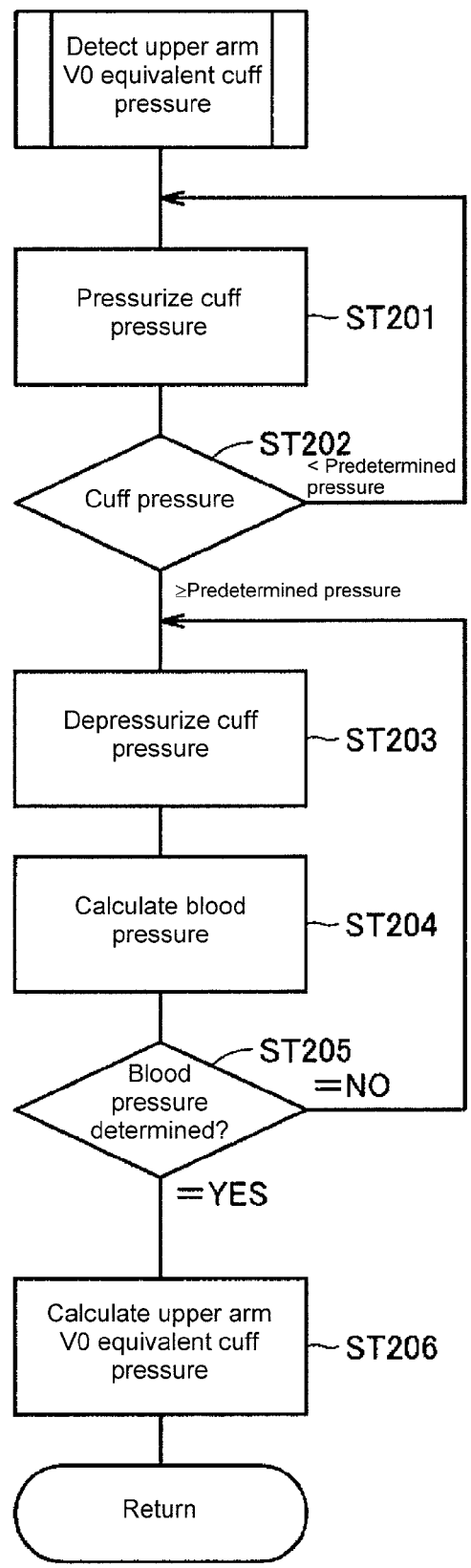
FIG. 7 is a flowchart showing the detection process of the upper arm V0 equivalent cuff pressure (upper arm equilibrium value) in the first embodiment of the present invention.

With reference to FIG. 7, the specifying unit 111 closes the valve 52B connected to the upper arm cuff 20B, and pressurizes the cuff pressure to a predetermined pressure (e.g., 180 mmHg) with the pump 51B (ST201, "<predetermined pressure" in ST202). Pressurization may be carried out up to systolic blood pressure (maximum blood pressure) estimated during the pressurization+predetermined value (e.g., 40 mmHg).

After pressurizing up to the predetermined pressure ("≥predetermined pressure" in ST202), the pump 51B is stopped and the valve 52B is gradually opened to gradually depressurize the cuff pressure (ST203).

The specifying unit 111 calculates the blood pressure through the oscillometric method in the process of gradual depressurization (ST204). Specifically, the pressure change (pressure pulse wave) involved in the arterial volume change superimposed on the cuff pressure is extracted. A predetermined algorithm is then applied on the extracted pressure pulse wave signal to calculate the blood pressure, that is, the systolic blood pressure and the diastolic blood pressure.

The depressurization is continued at a constant speed until the blood pressure is calculated (NO in ST205).

After the blood pressure is calculated (YES in ST205), the valve 52B is completely opened to exhaust the air in the cuff 20B. The average blood pressure is calculated as the upper arm V0 equivalent cuff pressure (ST206).

The average blood pressure is calculated with the following equation by the calculated systolic blood pressure and diastolic blood pressure.

Average blood pressure=diastolic blood pressure+ (systolic blood pressure−diastolic blood pressure)/3

The process returns to the main routine after the process of step ST206 is finished.

The blood pressure is calculated in the depressurization process in the present embodiment, but may be calculated in the pressurization process.

Figure 8:
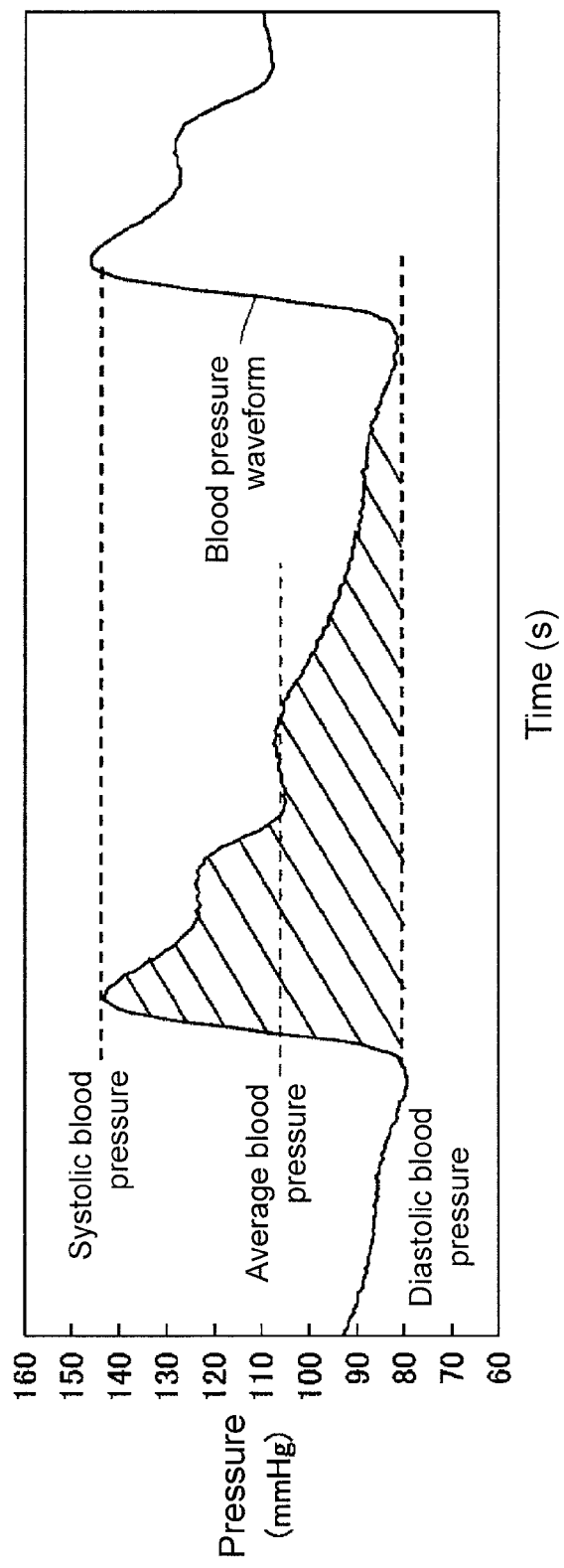
FIG. 8 is a view describing one example of a method for calculating the average blood pressure.

As shown in FIG. 8, the average blood pressure may be calculated by the areal mean of the blood pressure waveform for one beat of the pressure pulse wave amplitude. That is, the pressure value to become the average of the area of the shaded portion of FIG. 8 may be calculated as the average blood pressure.

In this case, the calculation process of the diastolic blood pressure and the systolic blood pressure as shown in the flowchart of FIG. 7 (ST204) is not necessary. Instead, a process of specifying the pressure pulse wave for one beat at the low cuff pressure (e.g., 30 mmHg) of lower than or equal to the diastolic blood pressure may be executed.

(Other Examples of Upper Arm V0 Equivalent Cuff Pressure Detection Process)

The average blood pressure is specified as the upper arm V0 equivalent cuff pressure in the above example, but is not limited thereto. For example, the cuff pressure at the time point when the maximum point of the pressure pulse wave amplitude is detected in the pressurization process may be detected as the upper arm V0 equivalent cuff pressure.

Figure 9:
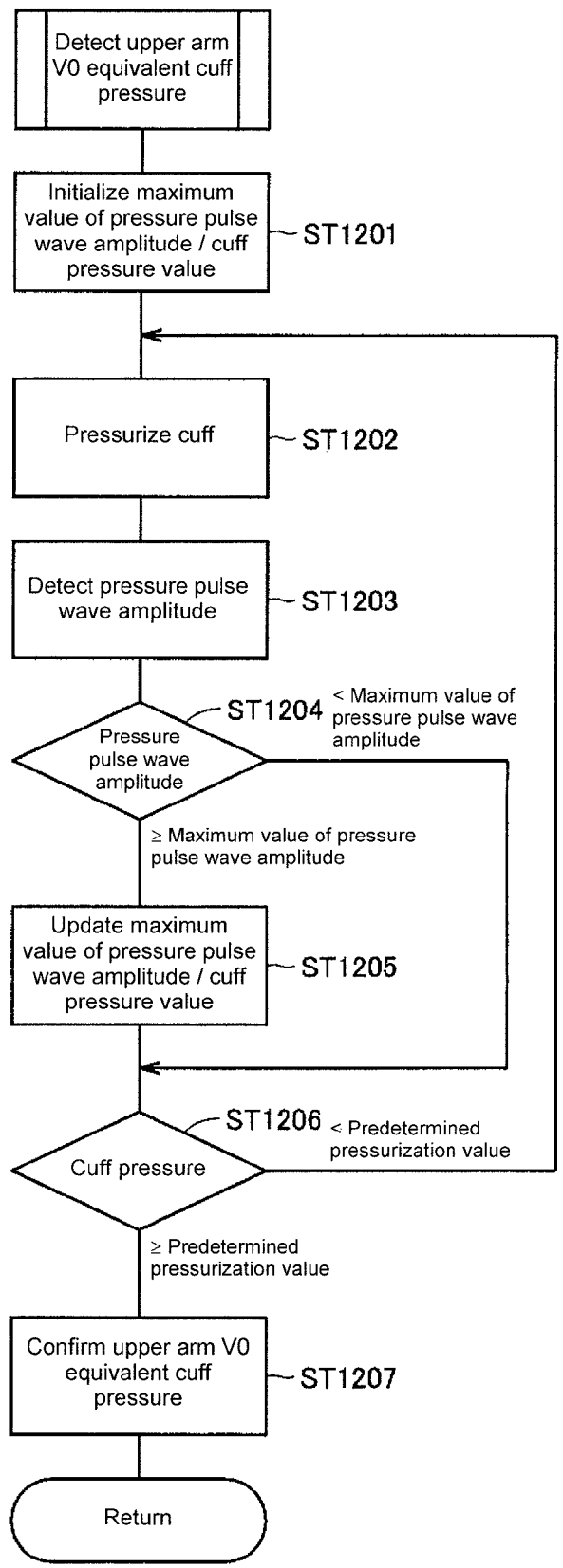
FIG. 9 is a flowchart showing another example of the detection process of the upper arm V0 equivalent cuff pressure in the first embodiment of the present invention.

With reference to FIG. 9, the memory region (e.g., predetermined region of memory unit 42) for storing the maximum value of the pressure pulse wave amplitude and the cuff pressure at the time is first initialized (ST1201).

The valve 52B connected to the upper arm cuff 20B is closed, and the pressure change (pressure pulse wave) involved in the arterial volume change superimposed on the cuff pressure is extracted while gradually pressurizing the cuff pressure with the pump 51B (ST1202, ST1203).

The specifying unit 111 determines whether or not the amplitude of the pressure pulse wave is a maximum (ST1204). If maximum ("≥maximum value of pressure pulse wave amplitude" in ST1204), the maximum value of the pressure pulse wave and the cuff pressure at the time are updated (ST1205). The process then proceeds to step ST1206.

If the pressure pulse wave amplitude is not a maximum ("<maximum value of pressure pulse wave amplitude" in ST1204), the process of step ST1205 is skipped, and the process proceeds to step ST1206.

In step ST1206, whether the cuff pressure reached a predetermined value (e.g., 180 mmHg) is determined. If determined that the cuff pressure has not reached the predetermined value ("<predetermined pressurization value" in ST1206), the process returns to step ST1202, and the above operation is repeated.

If the cuff pressure has reached the predetermined value ("≥predetermined pressurization value" in ST1206), the pump 51B is stopped and the valve 52B is opened to exhaust the air in the cuff 20B.

The specifying unit 111 confirms the cuff pressure obtained when the pressure pulse wave amplitude is a maximum as the upper arm V0 equivalent cuff pressure (ST1207). After such process is finished, the process is returned to the main routine.

In the present example, the maximum value of the pressure pulse wave amplitude is detected during pressurization, but may be detected during depressurization.

Figure 10:
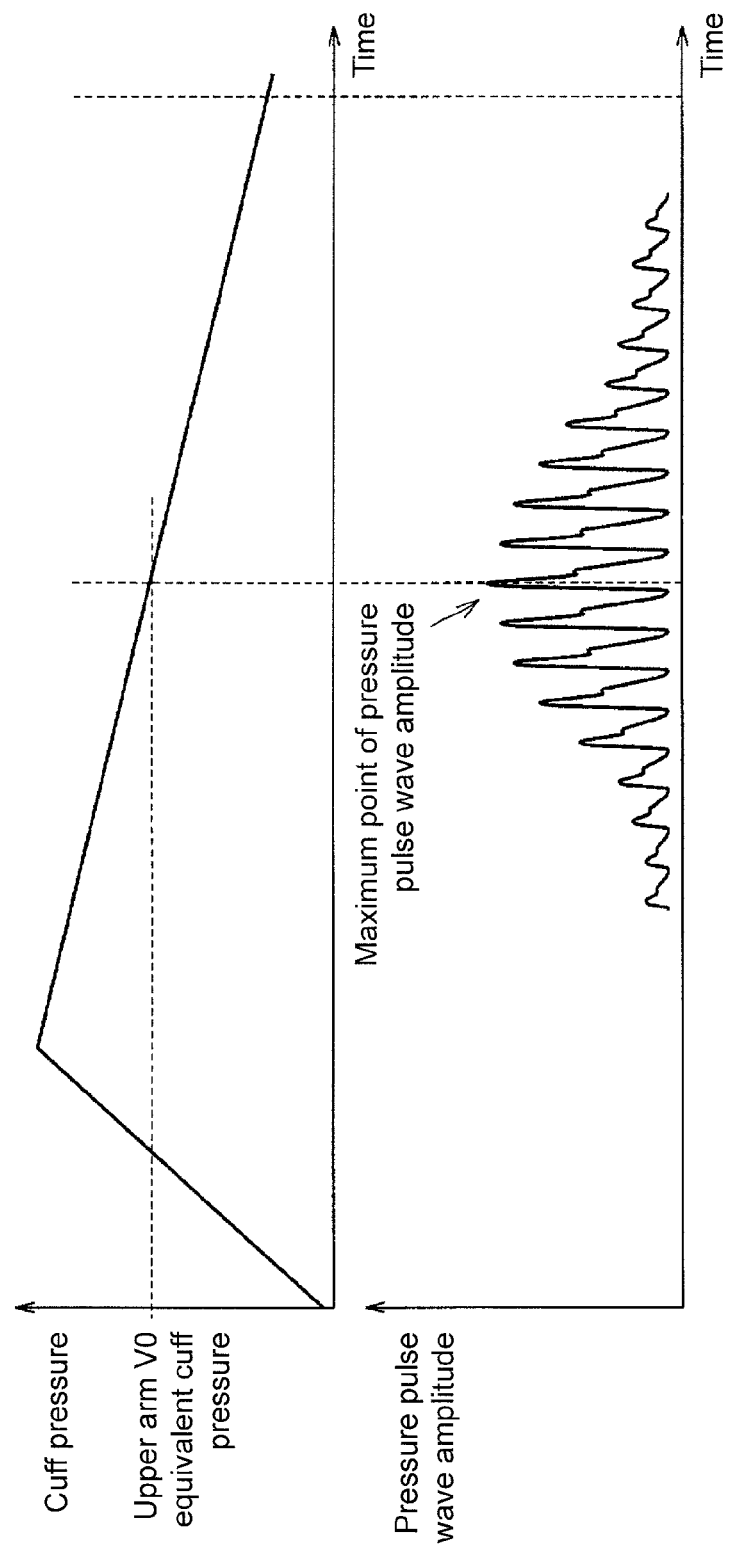
FIG. 10 is a view showing a relationship of the maximum value of the pressure pulse wave amplitude and the upper arm V0 equivalent cuff pressure.

FIG. 10 shows the upper arm V0 equivalent cuff pressure when the maximum value of the pressure pulse wave amplitude is detected during the depressurization. The cuff pressure when the pressure pulse wave amplitude is a maximum is substantially equal to the average blood pressure.

(Variant of First Embodiment)

In the first embodiment, the blood pressure is directly corrected by the difference (correction value) of the upper arm V0 equivalent cuff pressure and the control initial cuff pressure after the blood pressure is measured according to the volume compensation method through a known method.

In the present variant, on the other hand, the control target value and the control initial cuff pressure used in the arterial volume constant control are corrected to indirectly correct the blood pressure value that can be obtained according to the volume compensation method.

Only the portions different from the first embodiment will be hereinafter described.

Figure 11:
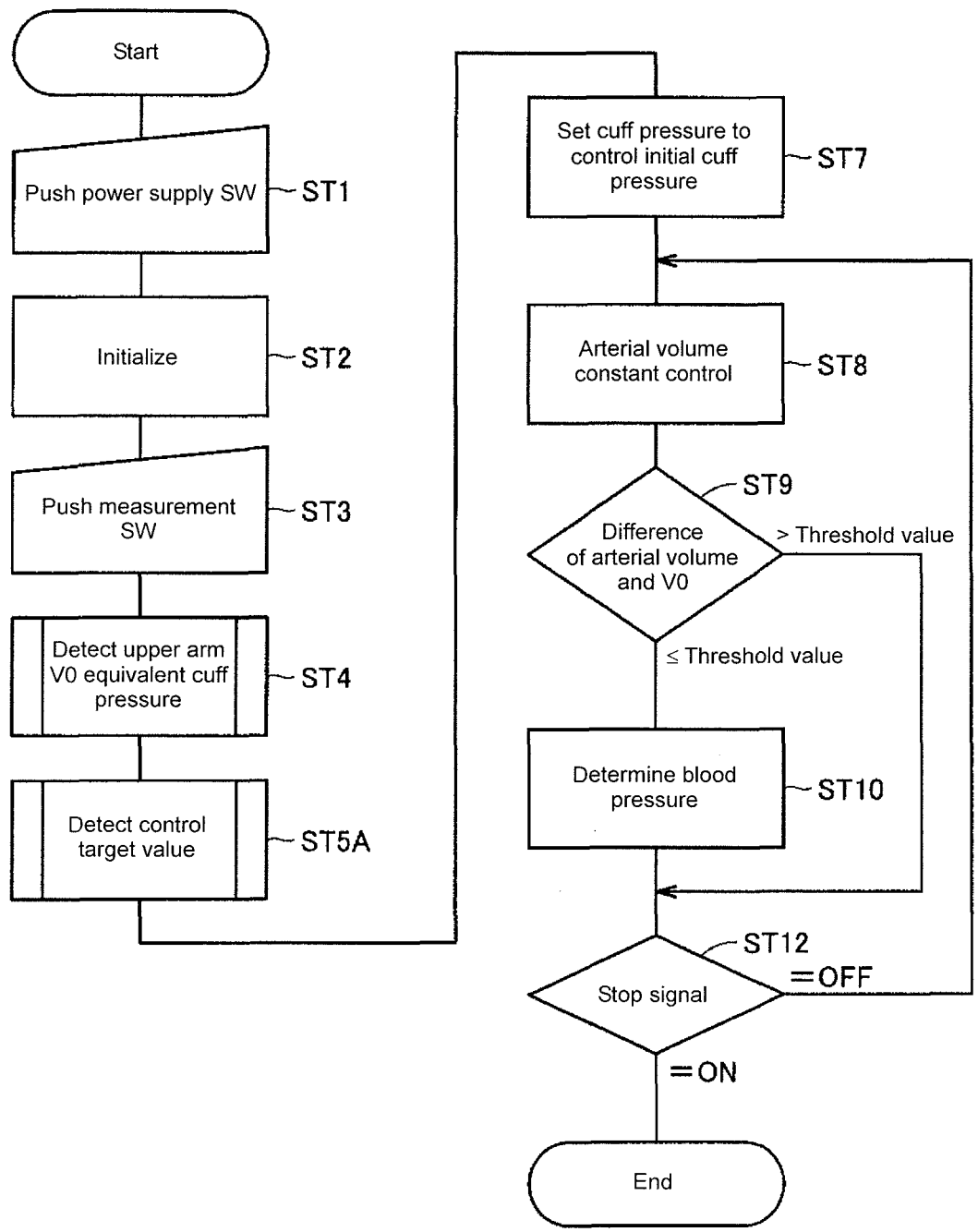
FIG. 11 is a flowchart showing the blood pressure measurement process according to a variant of the first embodiment of the present invention.

In the flowchart of FIG. 11 showing the blood pressure measurement process according to the variant of the first embodiment of the present invention, the same step numbers are denoted on the processes similar to the flowchart of FIG. 4. Thus, the description thereon will not be repeated.

With reference to FIG. 11, the control target value detection process differs in the present variant, and thus, the process of step ST5A is carried out in place of step ST5 in FIG. 4. The processes of steps ST6 and ST11 of FIG. 4 are not necessary.

The control target value detection process carried out in step ST5A will be described with reference to the flowchart of FIG. 12 and the graphs of FIG. 13. FIG. 13(A) shows the cuff pressure signal of the measurement cuff 20A along the time axis. FIG. 13(B) shows the arterial volume signal of the measurement site along the same time axis as FIG. 13(A).

Figure 12:
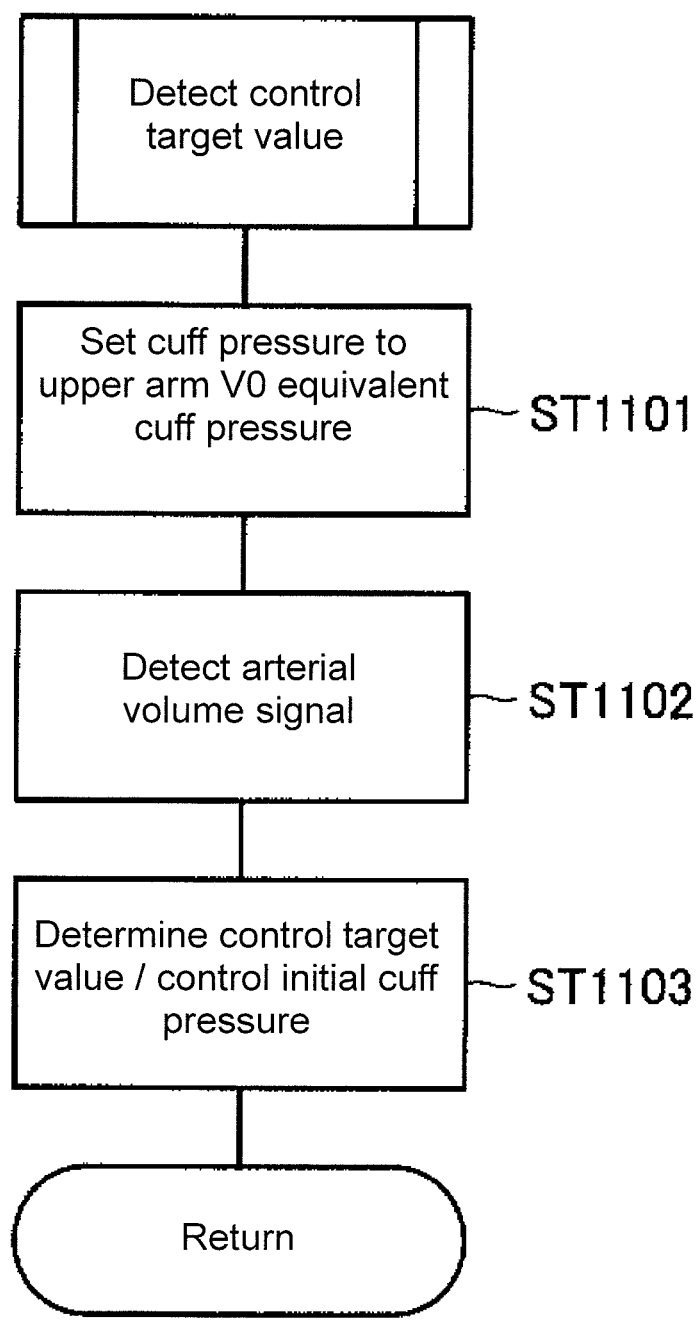
FIG. 12 is a flowchart showing the control target value detection process according to the variant of the first embodiment of the present invention.
Figure 13:
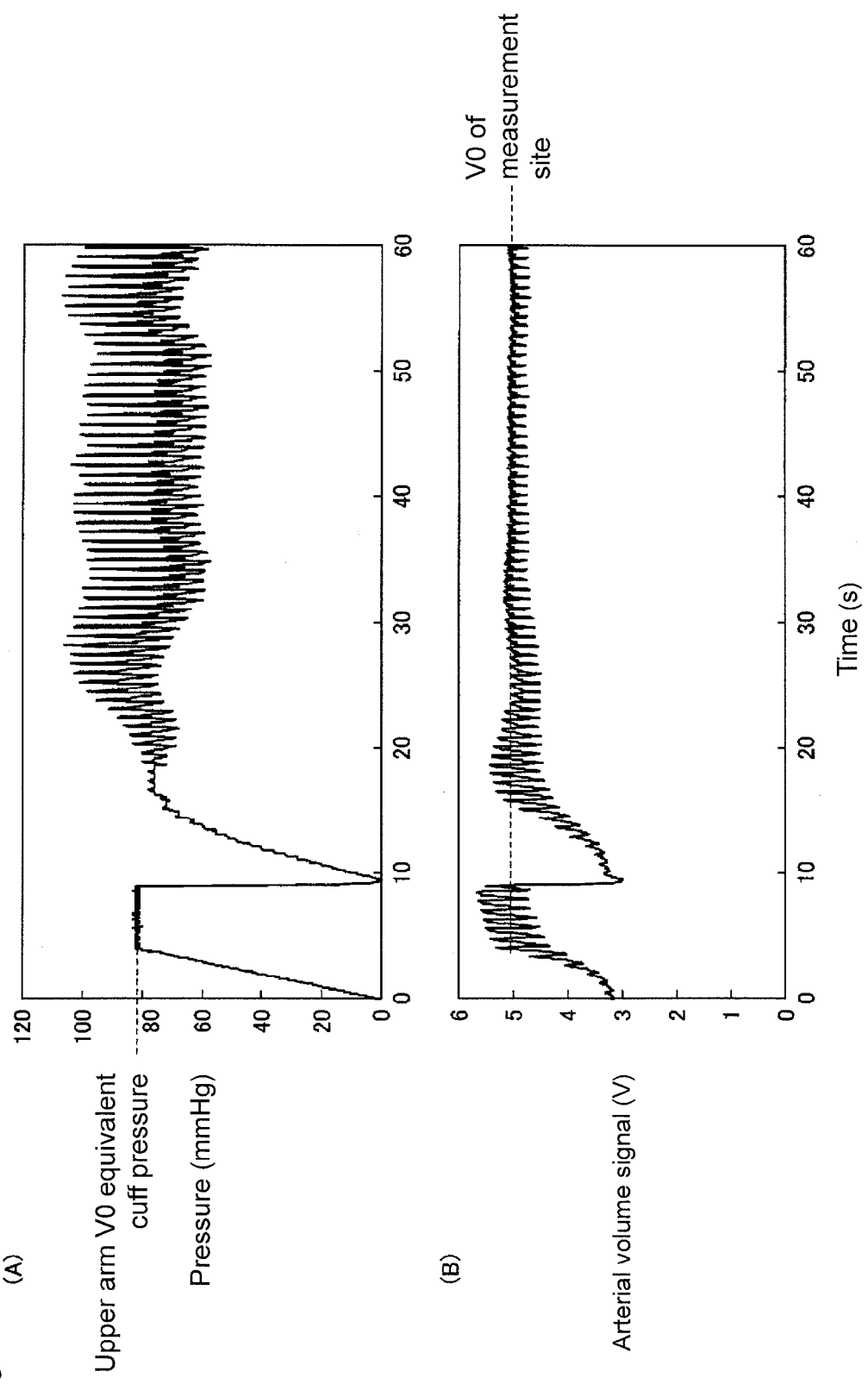
FIG. 13 is views for describing the method for determining the control target value and the control initial cuff pressure according to the variant of the first embodiment of the present invention.

With reference to FIG. 12 and FIG. 13(A), the measurement control unit 121 first sets the cuff pressure to the upper arm V0 equivalent cuff pressure detected in step ST4 (ST1101).

The arterial volume signal at the relevant time is then detected (ST1102), and the average value of the arterial volume signal for one beat is determined as the control target value (V0 of measurement site). The cuff pressure at the relevant time is determined as the control initial cuff pressure (ST1103). That is, the control initial cuff pressure and the upper arm V0 equivalent cuff pressure are equal in the present variant.

According to the variant of the present embodiment, the control target value is determined with the control initial cuff pressure as the upper arm V0 equivalent cuff pressure. That is, in the present variant, the control target value does not match with the value of the arterial volume in a state where the inner pressure and the outer pressure of the artery at the measurement site are in an equilibrium state if the height of the measurement site is shifted.

The error in pressure value caused by the shift in height of the measurement site and the heart can be reduced by feedback controlling the cuff pressure so as to match with the corrected control target value as in the present variant.

Furthermore, in the present variant, the control target value can be detected in a short time because the control initial cuff pressure is determined first. As a result, the continuous blood pressure measurement can be started faster than the first embodiment.

[Second Embodiment]

Then, a second embodiment of the present invention will be described below.

In the first embodiment and the variant thereof, the upper arm V0 equivalent cuff pressure is detected based on the pressure pulse wave signal of the upper arm cuff 20B. In the present embodiment, on the other hand, the upper arm V0 equivalent cuff pressure is detected based on the arterial volume signal through a method similar to detecting the control initial cuff pressure in the first embodiment.

The outer appearance, and the basic configuration and operation of the sphygmomanometer according to the present embodiment are similar to the first embodiment. Therefore, only the portions different from the first embodiment will be described below.

Figure 14:
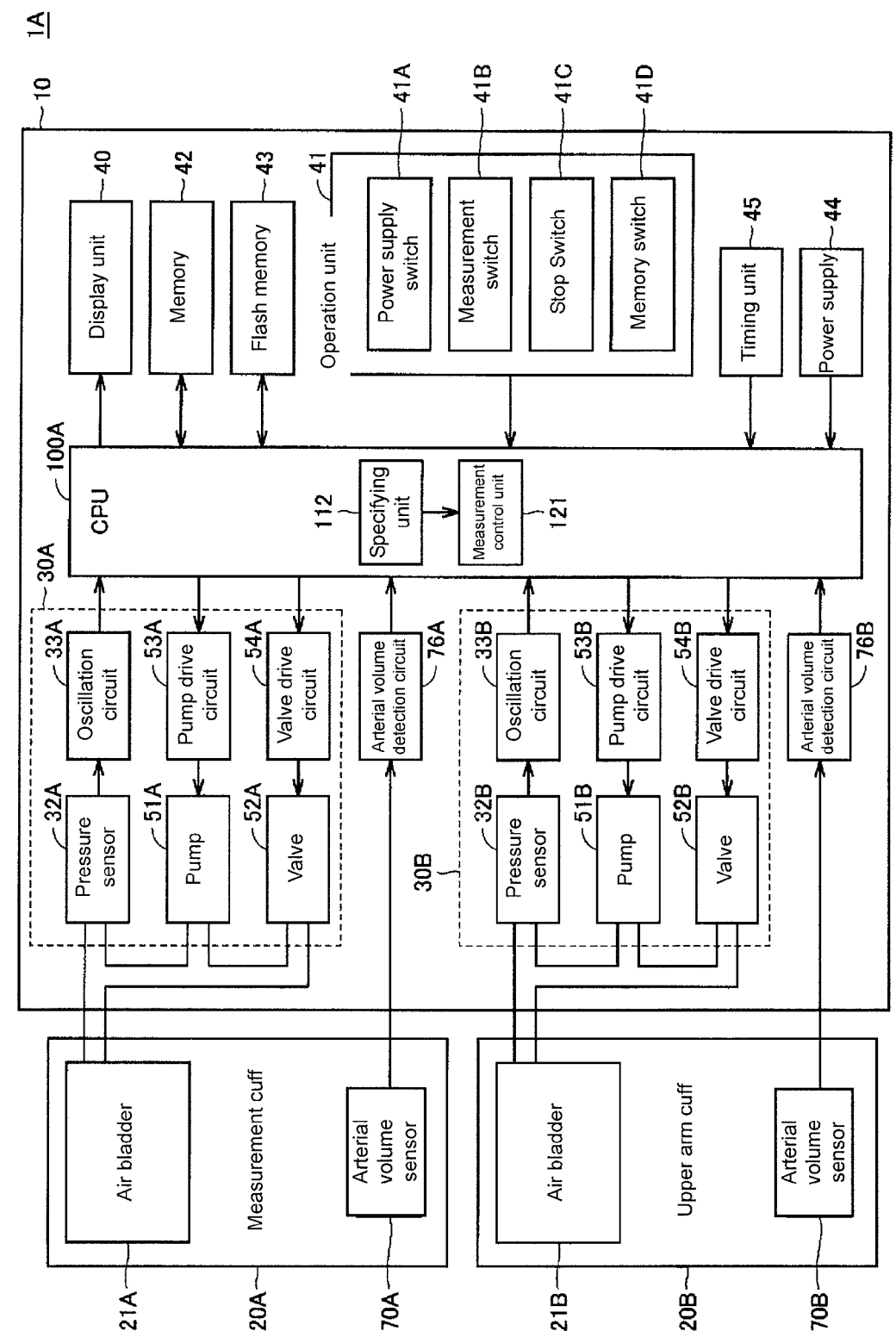
FIG. 14 is a block diagram showing a hardware configuration of a sphygmomanometer according to a second embodiment of the present invention.

FIG. 14 shows a hardware configuration of a sphygmomanometer 1A according to the second embodiment of the present invention.

With reference to FIG. 14, an arterial volume sensor 70B is also arranged in the upper arm cuff 20B in the present embodiment. Therefore, the arterial volume detection circuit 76B is also incorporated in the main body 10.

The configurations of the arterial volume sensor 70B and the arterial volume detection circuit 76B are similar to the arterial volume sensor 70A and the arterial volume detection circuit 76A in the measurement cuff 20A, respectively. Therefore, the description thereof will not be repeated.

In FIG. 14, a CPU 100A is shown in place of the CPU 100 because the functions executed by the CPU 100A of the sphygmomanometer 1A are different from the first embodiment.

The CPU 100A includes a specifying unit 112 in place of the specifying unit 111 of the first embodiment. The function of the measurement control unit 121 is similar to the first embodiment.

The specifying unit 112 detects the maximum value of the volume change signal of the upper arm based on the signal from the arterial volume detection circuit 76B. The cuff pressure at the time point when the maximum value of the volume change signal is detected is specified as the upper arm V0 equivalent cuff pressure.

The blood pressure measurement process according to the present embodiment is basically similar to the flowchart of FIG. 4 shown in the first embodiment. Only the detection process of the upper arm V0 equivalent cuff pressure executed in step ST5 of FIG. 4 is different.

Figure 15:
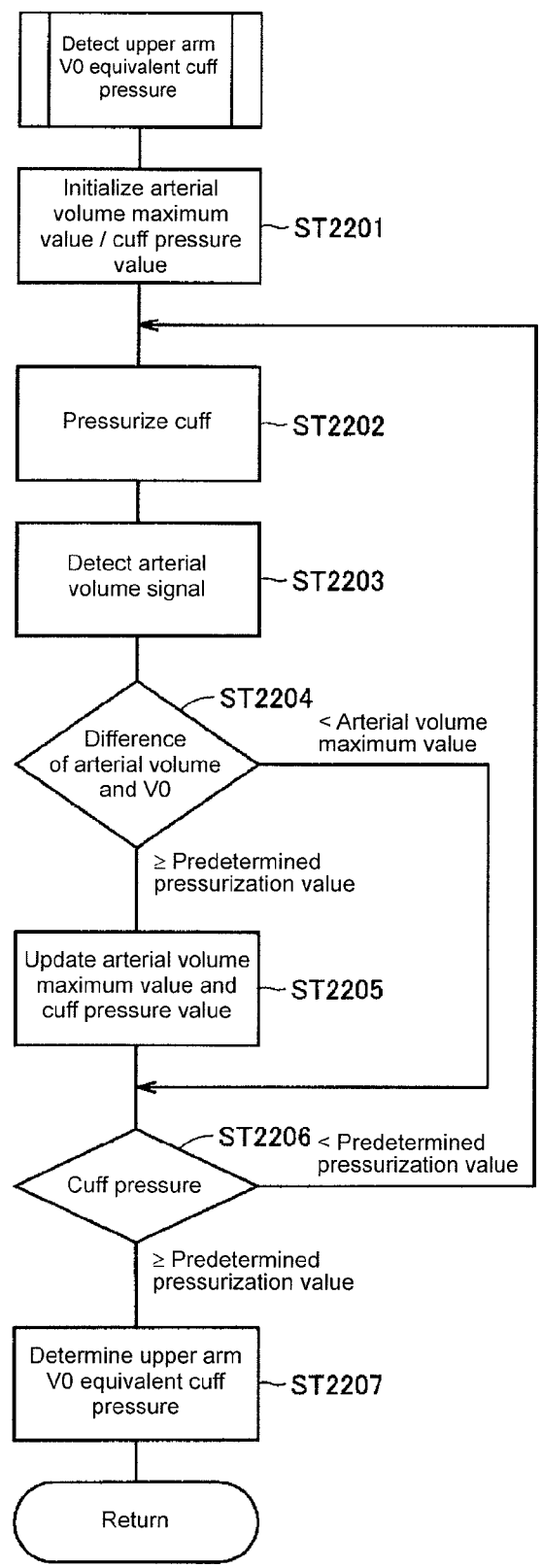
FIG. 15 is a flowchart showing a detection process of the upper arm V0 equivalent cuff pressure according to the second embodiment of the present invention.

The detection process of the upper arm V0 equivalent cuff pressure according to the present embodiment will be described with reference to the flowchart of FIG. 15.

First, the specifying unit 112 initializes a memory region (e.g., predetermined region of memory unit 42) for storing the maximum value of the arterial volume change of the upper arm and the cuff pressure at the relevant time (ST2201).

The valve drive circuit 54B is then drive-controlled to close the valve 52B, and the pump drive circuit 53B is drive-controlled to pressurize the pressure of the upper arm cuff 20B (ST2202).

During pressurization, the specifying unit 112 detects the signal (arterial volume signal) from the arterial volume detection circuit 76B (ST2203). Furthermore, the arterial volume change signal indicating the amount of change for every one beat of the arterial volume signal is detected. During the pressurization, for example, the value of the arterial volume signal is assumed to be stored in time series in correspondence with the cuff pressure.

The specifying unit 112 determines whether or not the detected arterial volume change is a maximum (ST2204). If determined that the detected arterial volume change is a maximum ("≥ maximum value of arterial volume change" in step ST2204), the maximum value of the arterial volume change and the cuff pressure at the relevant time are updated (ST2205). The process proceeds to step ST2206 after such process is finished.

If determined that the detected arterial volume change is not a maximum in step ST2204 ("<maximum value of arterial volume change" in ST2204), the process of step ST2205 is skipped and the process proceeds to step ST2206.

In step ST2206, the specifying unit 112 determines whether or not the cuff pressure is greater than or equal to a predetermined value (e.g., 180 mmHg). If determined that the cuff pressure has not reached the predetermined value ("<predetermined pressurization value" in ST2206), the process returns to step ST2202, and the above processes are repeated. If determined that the cuff pressure has reached the predetermined value ("≥predetermined pressurization value" in ST2206), the process proceeds to step ST2207.

In step ST2207, the specifying unit 112 determines the cuff pressure at the time point when the maximum value of the arterial volume is detected as the upper arm V0 equivalent cuff pressure. That is, the upper arm V0 equivalent cuff pressure represents the cuff pressure equivalent to (corresponding to) the average value (upper arm V0) of the arterial volume signal for one beat in which the amplitude is a maximum.

After the process of step ST2207 is finished, the process is returned to the main routine.

In the present embodiment, the maximum value of the arterial volume change is detected during the pressurization, but may be detected during the depressurization.

The measurement process according to the variant of the first embodiment and the upper arm V0 equivalent cuff pressure detection process of the present embodiment may be combined.

[Third Embodiment]

The sphygmomanometers in the first and second embodiments measure the blood pressure of the measurement site through the volume compensation method, but may measure the blood pressure through other methods as long as they are sphygmomanometers having the measurement site as the peripheral site.

The sphygmomanometer according to the present embodiment measures the blood pressure through the oscillometric method, for example.

The outer appearance, and the basic configuration and operation of the sphygmomanometer according to the present embodiment are similar to the first embodiment. Therefore, only the portions different from the first embodiment will be described below.

Figure 16:
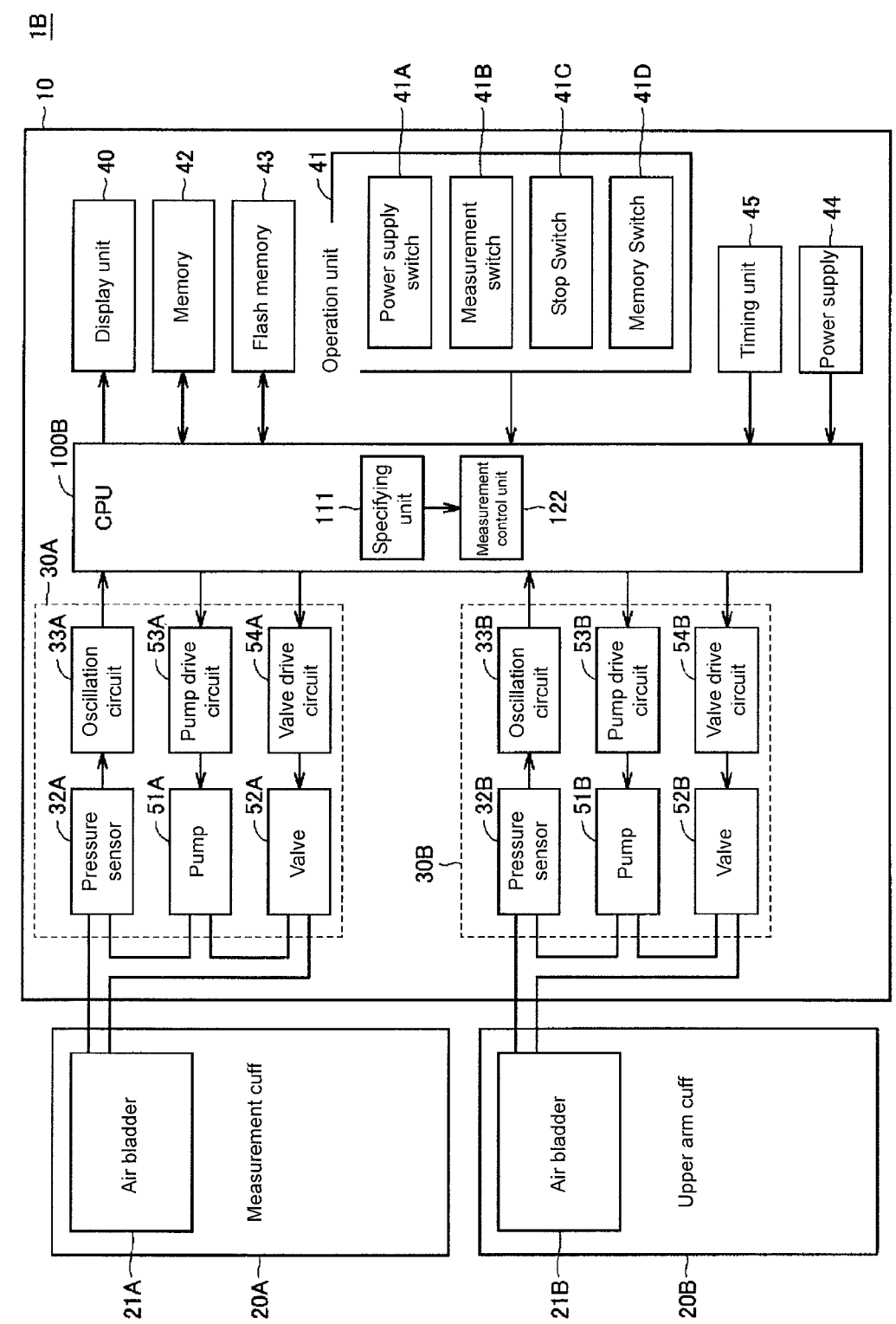
FIG. 16 is a block diagram showing a hardware configuration of a sphygmomanometer according to a third embodiment of the present invention.

FIG. 16 shows a hardware configuration of a sphygmomanometer 1B according to the present embodiment.

With reference to FIG. 16, the sphygmomanometer 1B according to the present embodiment does not include the arterial volume sensor 70A and the arterial volume detection circuit 76A.

In FIG. 16, a CPU 100B is shown in place of the CPU 100 because the functions executed by the CPU 100B of the sphygmomanometer 1B are different from the first embodiment.

The CPU 100B includes a measurement control unit 122 in place of the measurement control unit 121 of the first embodiment. The function of the specifying unit 111 is similar to the first embodiment.

The measurement control unit 122 calculates a temporary blood pressure value based on the amplitude of the pressure pulse wave of the measurement site obtained from the oscillation circuit 33A. The temporary blood pressure value is corrected according to the difference between the V0 equivalent cuff pressure of the measurement site and the upper arm V0 equivalent cuff pressure. In the present embodiment, the V0 equivalent cuff pressure of the measurement site can be specified through method similar to when the specifying unit 111 of the first embodiment specifies the upper arm V0 equivalent cuff pressure. That is, the V0 equivalent cuff pressure of the measurement site may represent one of the average blood pressures obtained from the cuff pressure signal of the measurement site, and the cuff pressure at the time point when the maximum value of the amplitude of the pressure pulse wave is detected.

Figure 17:
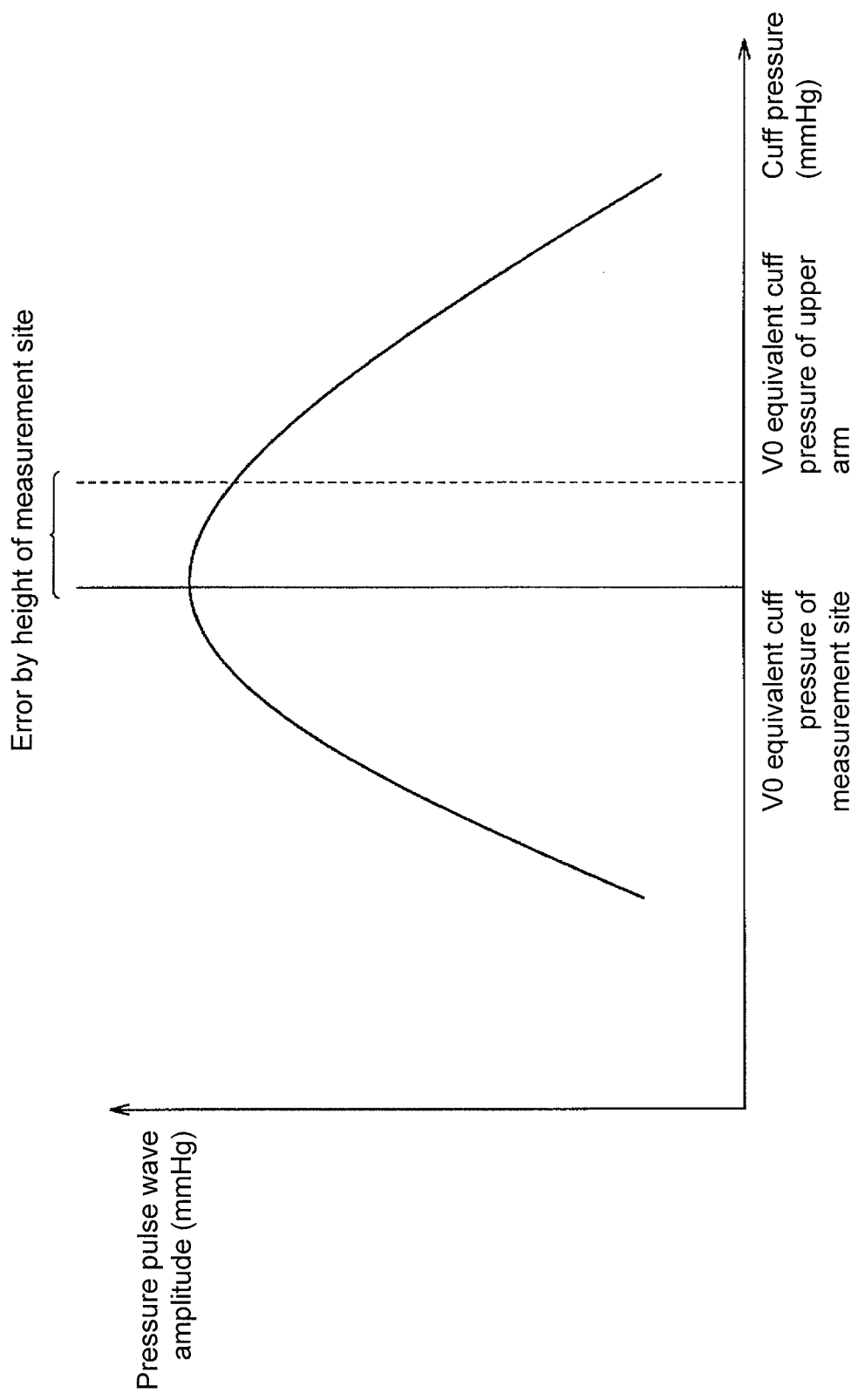
FIG. 17 is a view showing the concept of correcting the blood pressure according to the third embodiment of the present invention.

The concept of correcting blood pressure in the present embodiment will be briefly described with reference to FIG. 17.

When measuring the blood pressure through the oscillometric method, the envelope curve of the pressure pulse wave amplitude is used. The envelope curve of the pressure pulse wave amplitude of the measurement site does not match with the envelope curve of the pressure pulse wave amplitude of the upper arm if the height of the measurement site (e.g., wrist) is shifted from the height of the heart. Therefore, the upper arm V0 equivalent cuff pressure and the V0 equivalent cuff pressure of the measurement site do not match with each other.

Therefore, if the blood pressure is measured with the height of the measurement site shifted, the error occurs in the measurement value by the difference between the upper arm V0 equivalent cuff pressure and the V0 equivalent cuff pressure of the measurement site. Thus, in the present embodiment as well, the difference between the upper arm V0 equivalent cuff pressure and the V0 equivalent cuff pressure of the measurement site, which becomes the cause of error, is used for the correction of the blood pressure.

Figure 18:
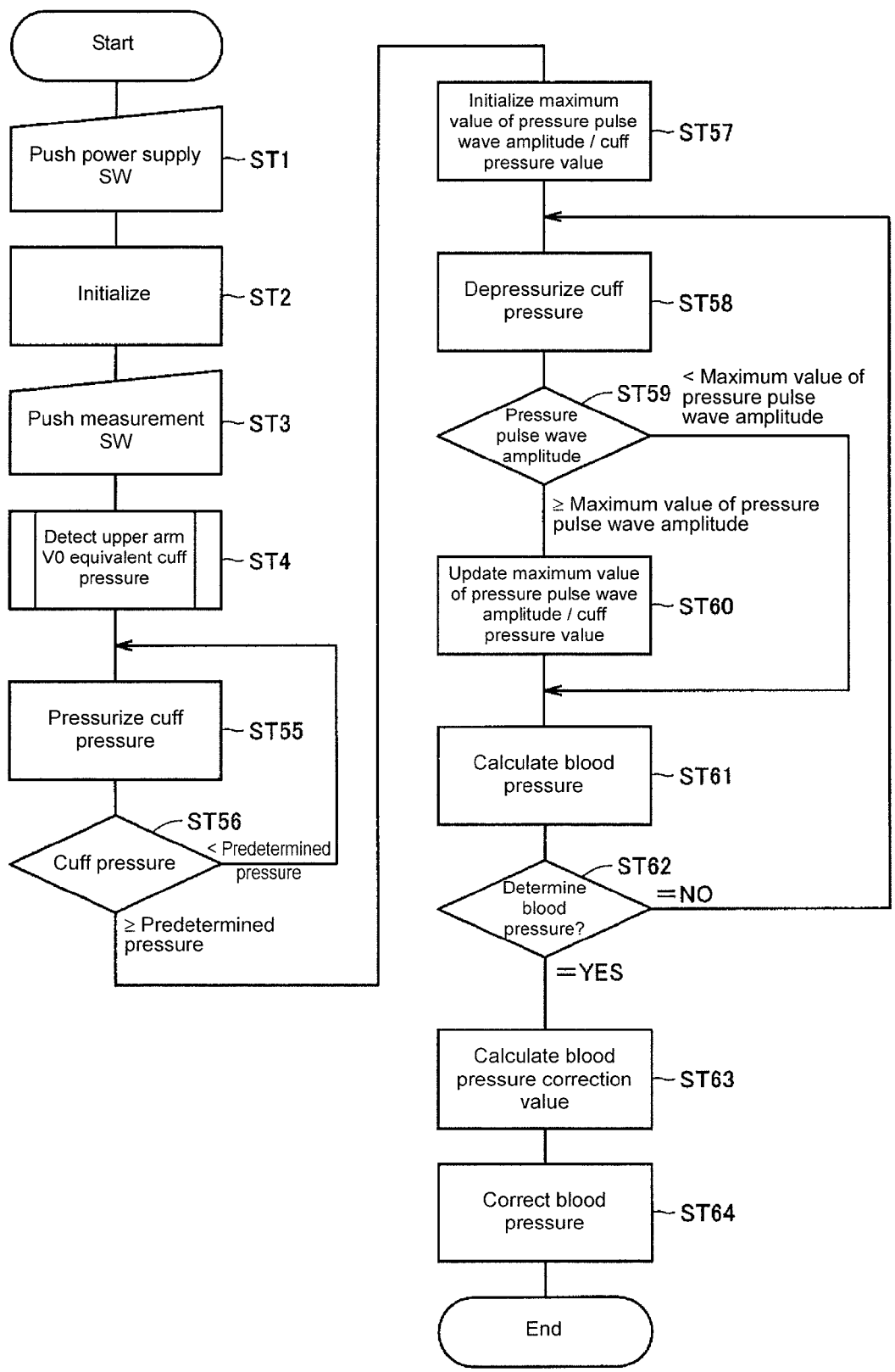
FIG. 18 is a flowchart showing a blood pressure measurement process in the third embodiment of the present invention.

The blood pressure measurement process in the present embodiment will be described using the flowchart of FIG. 18. In FIG. 18, the same step numbers are denoted for the processes similar to the flowchart of FIG. 4. The description thereof thus will not be repeated.

In the present embodiment, the start of flow to the detection of the upper arm V0 equivalent cuff pressure (ST4) is similar to the first embodiment, but differs in the subsequent processes.

With reference to FIG. 18, when the upper arm V0 equivalent cuff pressure is detected, the measurement control unit 122 closes the valve 52A connected to the measurement cuff 20A, and pressurizes the cuff pressure up to a predetermined pressure (e.g., 180 mmHg) with the pump 51A (ST55, "<predetermined pressure" in ST56). In this case as well, pressurization may be carried out up to the systolic blood pressure (maximum blood pressure) estimated during the pressurization+predetermined value (e.g., 40 mmHg).

After pressurizing up to the predetermined pressure ("≥predetermined pressure" in ST56), the memory region (e.g., predetermined region of memory unit 42) for storing the maximum value of the pressure pulse wave amplitude and the cuff pressure at the time is first initialized (ST57). The pump 51A is then stopped and the valve 52A is gradually opened to gradually depressurize the cuff pressure (ST58).

The measurement control unit 122 calculates the blood pressure through the oscillometric method in the gradually depressurizing process (ST59 to ST61). Specifically, the pressure change (pressure pulse wave) involved in the arterial volume change superimposed on the cuff pressure is extracted. If the amplitude of the extracted pressure pulse wave is a maximum ("≥maximum value of pressure pulse wave amplitude" in ST59), the maximum value of the pressure pulse wave amplitude and the cuff pressure at the relevant time are updated (ST60).

The measurement control unit 122 then executes the blood pressure calculation process (ST61). The calculation of the blood pressure is carried out based on the relationship of the envelope curve of the amplitude value of the pressure pulse wave and the cuff pressure.

The above processes (ST58 to ST61) are repeated until the blood pressures (systolic blood pressure and diastolic blood pressure) are determined (NO in ST62).

After the blood pressures are determined, the measurement control unit 122 calculates the blood pressure correction value (ST62). The blood pressure correction value is calculated with the following equation.

Correction value=*V*0 equivalent cuff pressure of measurement site−upper arm *V*0 equivalent cuff pressure The V0 equivalent cuff pressure of the measurement site may be, for example, the cuff pressure value obtained when the pressure pulse wave amplitude is a maximum (value stored in ST60). It may be a value equivalent to the average blood pressure.

Lastly, the blood pressure value calculated in step ST61 is corrected by the blood pressure correction value obtained in step ST63 (ST64). The correction of the blood pressure is carried out with the following equation.

Blood pressure value=Blood pressure−correction value

In the present embodiment, the correction value is subtracted from the respective value in step ST64 because the systolic blood pressure and the diastolic blood pressure are measured.

In the present embodiment, the blood pressure is calculated in the depressurization process, but the blood pressure may be calculated in the pressurization process.

The error in measurement value due to the difference in measurement site (upper arm and peripheral site) can be reduced even with the sphygmomanometer that complies with the oscillometric method, as described above.

The oscillometric method is used in the present embodiment, but other blood pressure calculation methods such as the Korotkoff sound method and the volume vibration method may be used.

(Variant)

The blood pressure measurement process according to the present embodiment and the upper arm V0 equivalent cuff pressure detection process according to the second embodiment may be combined. The hardware configuration of the sphygmomanometer in such case is shown in FIG. 19.

Figure 19:
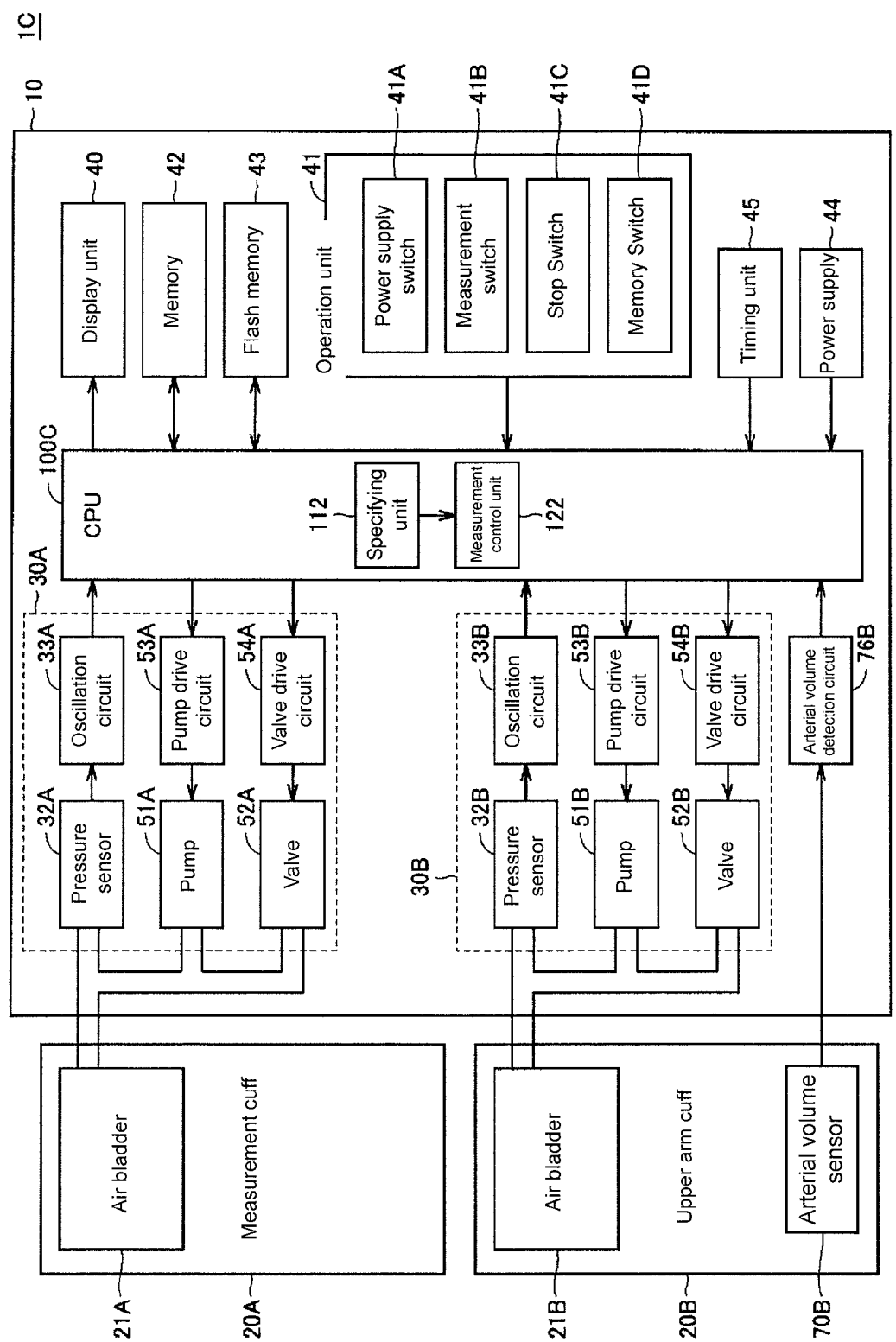
FIG. 19 is a block diagram showing a hardware configuration of a sphygmomanometer according to a variant of the third embodiment of the present invention.

With reference to FIG. 19, a sphygmomanometer 1C according to the present embodiment includes an arterial volume sensor 70B and an arterial volume detection circuit 76B, similar to the sphygmomanometer 1A of the second embodiment.

In FIG. 19, a CPU 100C is shown in place of the CPU 100B because the functions executed by the CPU 100C of the sphygmomanometer 1C are different from the third embodiment.

The CPU 100C includes the specifying unit 112 described in the second embodiment and the measurement control unit 122 described in the third embodiment. The specifying unit 112 specifies the upper arm V0 equivalent cuff pressure through a method similar to the control initial cuff pressure detection of arterial volume constant control. The measurement control unit 122 measures the (temporary) blood pressure according to the oscillometric method, and corrects the measured blood pressure with the upper arm V0 equivalent cuff pressure. The functions of the specifying unit 112 and the measurement control unit 122 are already described, and hence, the detailed description thereof will not be repeated.

Therefore, in each embodiment and each variant of the present invention, the error in measurement value caused by the shift in height of the measurement site (peripheral site) can be reduced by using the upper arm V0 equivalent cuff pressure.

Furthermore, the error caused by biological factors of the peripheral site (in particular, wrist) can be resolved by carrying out the correction control of the blood pressure of the peripheral site using the upper arm V0 equivalent cuff pressure. This will be specifically described.

Figure 20:
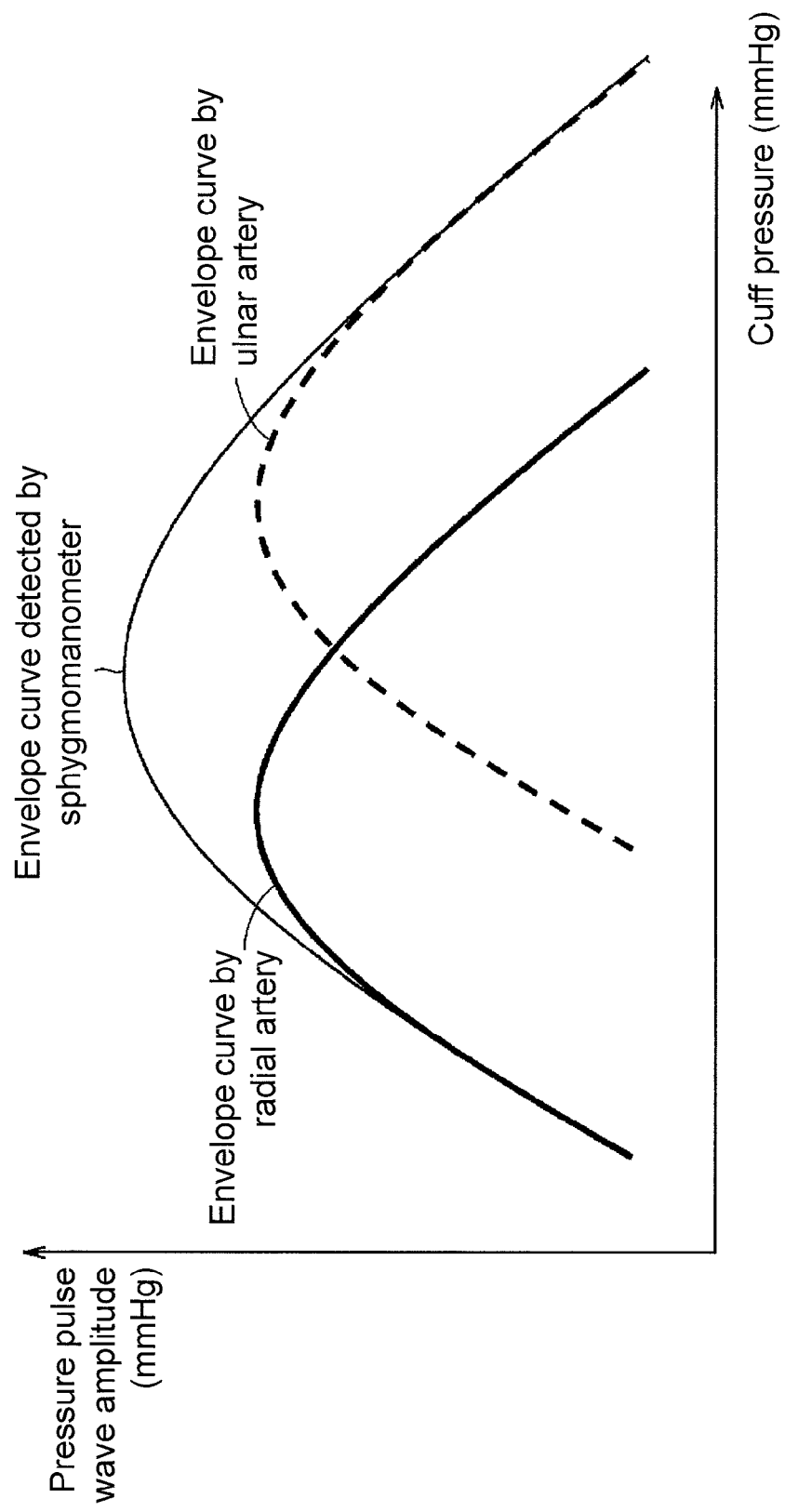
FIG. 20 is a view describing the error in blood pressure caused by physiological factors of the peripheral site (in particular, wrist).

Two arteries run through the wrist. The artery running along the thumb side of the wrist is called the radial artery, and the artery running along the small finger side is called the ulnar artery. Regarding the depth at which the two arteries are running (depth from the surface of the wrist), the radial artery is generally running through a position shallower than the ulnar artery. Obviously, the depth of the position at which the artery is running and the difference in depth of the radial artery and the ulnar artery differ among people. Therefore, if the wrist is compressed with the cuff, two envelope curves of the pulse wave amplitude are detected if the artery is viewed individually, as shown in FIG. 20, because the pressure transmitted to the two arteries differs among people. The envelope curve actually detected by the sphygmomanometer is the sum of the two envelope curves, and hence, the blood pressure may not be correctly measured.

At the upper arm, on the other hand, the blood pressure is calculated based on one envelope curve, and hence, the error due to physiological factors of the measurement site does not occur. Therefore, according to each embodiment and each variant of the present invention, the error in measurement value due to such physiological factors can also be resolved.

In each embodiment and each variant, the calculation of the correction value, and the like are carried out for every measurement because the shift in height is being focused. However, if only the physiological factor is being focused, the once calculated correction value may be stored and the blood pressure may be corrected based on the stored correction value in the subsequent processes.

While the invention has been described with respect to a limited number of embodiments, those skilled in the art, having the benefit of this disclosure, will appreciate that other embodiments can be devised which do not depart from the scope of the invention as disclosed herein. Accordingly, the scope of the invention should be limited only by the attached claims.

DESCRIPTION OF REFERENCE NUMERALS

1, 1A, 1B, 1C electronic sphygmomanometer
10 main body
20A, 20B cuff
21A, 21B air bladder
30A, 30B air system
31A, 31B air tube
32A, 32B pressure sensor
33A, 33B oscillation circuit
40 display unit
41 operation unit
41A power supply switch
41B measurement switch
41C stop switch
41D memory switch
42 memory unit
43 flash memory
44 power supply
45 timing unit
51A, 51B pump
52A, 52B valve
53A, 53B pump drive circuit
54A, 54B valve drive circuit
70A, 70B arterial volume sensor
76A, 76B arterial volume detection circuit
100, 100A, 100B, 100C CPU
111, 112 specifying unit
121, 122 measurement control unit

The invention claimed is:

1. An electronic sphygmomanometer comprising:
   a first cuff configured to be wrapped around a peripheral site,
      wherein the peripheral site is a measurement site;
   a second cuff to be wrapped around an upper arm;
   a pressure detection unit that detects a first cuff pressure signal representing a pressure of the first cuff and a second cuff pressure signal representing a pressure of the second cuff;
   a specific processing unit that carries out a process that specifies an upper arm V0 equivalent cuff pressure representing a cuff pressure in a state where an inner pressure and an outer pressure of an artery of the upper arm are in equilibrium based on the second cuff pressure signal;

a measurement control unit that measures a blood pressure of a person to be measured based on the first cuff pressure signal; and a first volume detection unit arranged at a predetermined position of the first cuff, that detects a first arterial volume signal at the peripheral site, wherein the measurement control unit carries out a control that corrects a blood pressure value through a first calculation using control initial cuff pressure, which represents a cuff pressure in a state where an inner pressure and an outer pressure of an artery of the peripheral site are in equilibrium, and the upper arm V0 equivalent cuff pressure, so as to obtain a correction value such that:

the correction value=the control initial cuff pressure−
the upper arm *V*0 equivalent cuff pressure, and through a second calculation using a volume compensation method blood pressure obtained according to the first cuff pressure signal, and the correction value, so as to obtain a corrected blood pressure such that:

the corrected blood pressure value=the volume compensation method blood pressure−the correction value, wherein the measurement control unit carries out an arterial volume constant control based on the first arterial volume signal to continuously measure the blood pressure, wherein the control initial cuff pressure corresponds to an initial cuff pressure representing a reference value of the first cuff pressure signal in the arterial volume constant control, and wherein the measurement control unit:

detects a maximum value of a volume change signal of the peripheral site from the first arterial volume signal in a process of gradually pressurizing or depressurizing the pressure of the first cuff to detect a volume value in a state where the inner pressure and the outer pressure of the artery of the peripheral site are in equilibrium as a control target value in the arterial volume constant control and to detect a value of the first cuff pressure signal corresponding to a time point when the control target value is detected as the initial cuff pressure;

determines the cuff pressure obtained when a difference between the value of the first arterial volume signal and the control target value becomes smaller than or equal to a predetermined value when the arterial volume constant control is carried out, as a temporary blood pressure value; and corrects the temporary blood pressure value according to a difference between the upper arm V0 equivalent cuff pressure and the initial cuff pressure.

2. The electronic sphygmomanometer according to claim 1, wherein the specific processing unit specifies either an average blood pressure obtained from the second cuff pressure signal or the cuff pressure at a time point when a maximum value of an amplitude of a pressure pulse wave is detected, as the upper arm V0 equivalent cuff pressure.

3. The electronic sphygmomanometer according to claim 1, further comprising:

a second volume detection unit, arranged at a predetermined position of the second cuff, that detects a second arterial volume signal at the upper arm, wherein the specific processing unit specifies the upper arm V0 equivalent cuff pressure by detecting a maximum value of an arterial volume change of the upper arm from the second arterial volume signal in a process of gradually pressurizing or depressurizing the pressure of the second cuff.

\* \* \* \* \*